(12) United States Patent
Toida et al.

(10) Patent No.: US 10,745,372 B2
(45) Date of Patent: Aug. 18, 2020

(54) COMPOUND, RESIN, MATERIAL FOR FORMING UNDERLAYER FILM FOR LITHOGRAPHY, UNDERLAYER FILM FOR LITHOGRAPHY, PATTERN FORMING METHOD, AND PURIFICATION METHOD

(71) Applicant: Mitsubishi Gas Chemical Company, Inc., Tokyo (JP)

(72) Inventors: Takumi Toida, Kanagawa (JP); Masatoshi Echigo, Tokyo (JP); Takashi Sato, Kanagawa (JP); Takashi Makinoshima, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/539,560

(22) PCT Filed: Dec. 14, 2015

(86) PCT No.: PCT/JP2015/084907
§ 371 (c)(1),
(2) Date: Jun. 23, 2017

(87) PCT Pub. No.: WO2016/104214
PCT Pub. Date: Jun. 30, 2016

(65) Prior Publication Data
US 2017/0349564 A1 Dec. 7, 2017

(30) Foreign Application Priority Data
Dec. 25, 2014 (JP) .................................. 2014-262564

(51) Int. Cl.
| | | |
|---|---|---|
| *G03F 7/11* | (2006.01) | |
| *G03F 7/20* | (2006.01) | |
| *G03F 7/30* | (2006.01) | |
| *G03F 7/16* | (2006.01) | |
| *C07D 311/78* | (2006.01) | |
| *C09D 161/06* | (2006.01) | |
| *C08G 8/08* | (2006.01) | |
| *C08G 8/04* | (2006.01) | |
| *C08G 18/30* | (2006.01) | |

(52) U.S. Cl.
CPC .............. *C07D 311/78* (2013.01); *C08G 8/08* (2013.01); *C09D 161/06* (2013.01); *G03F 7/11* (2013.01); *G03F 7/16* (2013.01); *G03F 7/20* (2013.01); *G03F 7/30* (2013.01)

(58) Field of Classification Search
CPC . C07D 311/78; G03F 7/20; G03F 7/11; G03F 7/16; G03F 7/26; G03F 7/30; G08G 8/08; G08G 18/30; G08G 8/04; C09D 161/06
See application file for complete search history.

(56) References Cited

U.S. PATENT DOCUMENTS

| | | | |
|---|---|---|---|
| 2,100,798 A | 11/1937 | Dilthey | |
| 2,546,872 A | 3/1951 | Schmid | |
| 2,587,437 A | 2/1952 | Bralley | |
| 3,947,468 A | 3/1976 | Hall | |
| 4,252,884 A | 2/1981 | Bennett | |
| 4,289,839 A | 9/1981 | Dipippo | |
| 4,482,489 A | 11/1984 | Dipippo | |
| 4,579,758 A | 4/1986 | Dorsch | |
| 5,332,648 A | 7/1994 | Kihara | |
| 5,986,094 A | 11/1999 | Ghoshal | |
| 6,784,228 B2 * | 8/2004 | Ogura .................. | C07D 311/78 523/466 |
| 6,794,408 B2 * | 9/2004 | Eder .................... | C07D 307/77 252/404 |
| 7,871,751 B2 | 1/2011 | Echigo | |
| 9,136,121 B2 * | 9/2015 | Hatakeyama ........... | G03F 7/094 |

(Continued)

FOREIGN PATENT DOCUMENTS

| | | |
|---|---|---|
| CN | 1414031 | 4/2003 |
| CN | 1853141 A | 10/2006 |

(Continued)

OTHER PUBLICATIONS

Ghodratbeigi et al., "Design modeling and synthesis of molecular tweezers with self assembly properties", J. Mol. Struct., vol. 990 pp. 140-151 (2011).*

(Continued)

*Primary Examiner* — Martin J Angebranndt
(74) *Attorney, Agent, or Firm* — Fitch, Even, Tabin & Flannery LLP

(57) ABSTRACT

A compound represented by the following formula (1):

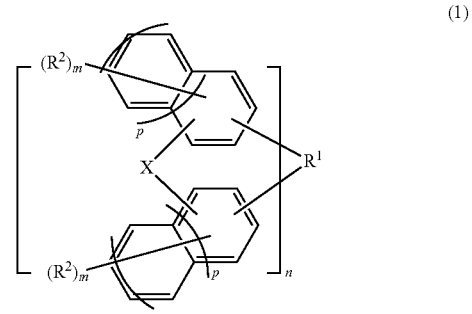

wherein each X independently represents an oxygen atom or a sulfur atom, or non-crosslinking, $R^1$ represents a single bond or a 2n-valent group having 1 to 30 carbon atoms, the group may have an alicyclic hydrocarbon group, a double bond, a hetero atom, or an aryl group having 6 to 30 carbon atoms, each $R^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one $R^2$ represents an alkoxy group having 1 to 30 carbon atoms or an aryloxy group having 6 to 30 carbon atoms, each m is independently an integer of 1 to 6, each p is independently 0 or 1, and n is an integer of 1 to 4.

11 Claims, No Drawings

(56) References Cited

U.S. PATENT DOCUMENTS

| | | | |
|---|---|---|---|
| 9,274,426 B2* | 3/2016 | Rahman | G03F 7/091 |
| 9,316,913 B2 | 4/2016 | Echigo | |
| 9,540,339 B2 | 1/2017 | Echigo | |
| 9,908,831 B2 | 3/2018 | Echigo | |
| 10,303,055 B2 | 5/2019 | Sato | |
| 10,377,734 B2 | 8/2019 | Echigo | |
| 2002/0106909 A1 | 8/2002 | Kato | |
| 2003/0092852 A1 | 5/2003 | Ogura | |
| 2004/0197709 A1 | 10/2004 | Arase | |
| 2005/0074695 A1 | 4/2005 | Nakamura | |
| 2005/0255712 A1 | 11/2005 | Kato et al. | |
| 2007/0059632 A1 | 3/2007 | Oguro | |
| 2007/0172759 A1 | 7/2007 | Ogihara | |
| 2007/0232839 A1 | 10/2007 | Yoshitomo | |
| 2007/0275325 A1* | 11/2007 | Hatakeyama | C08G 8/20 430/270.1 |
| 2008/0113294 A1 | 5/2008 | Echigo | |
| 2008/0138744 A1 | 6/2008 | Hatanaka | |
| 2008/0153031 A1 | 6/2008 | Echigo | |
| 2009/0171061 A1 | 7/2009 | Sue | |
| 2009/0246684 A1 | 10/2009 | Kim | |
| 2009/0261300 A1 | 10/2009 | Watanabe | |
| 2010/0047709 A1 | 2/2010 | Echigo | |
| 2010/0099044 A1 | 4/2010 | Hatakeyama | |
| 2010/0104977 A1 | 4/2010 | Hatakeyama | |
| 2010/0136477 A1 | 6/2010 | Ng | |
| 2010/0190107 A1 | 7/2010 | Shibata | |
| 2010/0207516 A1 | 8/2010 | Moriwaki | |
| 2010/0227859 A1 | 9/2010 | Li | |
| 2010/0285407 A1 | 11/2010 | Ogihara | |
| 2010/0316950 A1 | 12/2010 | Oguro et al. | |
| 2011/0177459 A1 | 7/2011 | Ogihara | |
| 2011/0274713 A1 | 11/2011 | Burn | |
| 2011/0311920 A1 | 12/2011 | Kinsho | |
| 2012/0064725 A1 | 3/2012 | Kinsho | |
| 2012/0171611 A1 | 7/2012 | Ideno et al. | |
| 2012/0184103 A1 | 7/2012 | Ogihara | |
| 2012/0220112 A1 | 8/2012 | Hatakeyama | |
| 2012/0228584 A1 | 9/2012 | Wigglesworth | |
| 2013/0004896 A1 | 1/2013 | Echigo et al. | |
| 2013/0056653 A1 | 3/2013 | Hatakeyama | |
| 2013/0087529 A1 | 4/2013 | Hatakeyama et al. | |
| 2013/0150627 A1 | 6/2013 | Okada | |
| 2014/0186776 A1 | 7/2014 | Uchiyama | |
| 2014/0248556 A1 | 9/2014 | Kato et al. | |
| 2014/0248561 A1 | 9/2014 | Echigo | |
| 2014/0308615 A1 | 10/2014 | Echigo | |
| 2014/0319097 A1 | 10/2014 | Kim | |
| 2014/0363768 A1 | 12/2014 | Kinsho et al. | |
| 2014/0363955 A1 | 12/2014 | Hatakeyama et al. | |
| 2014/0363957 A1* | 12/2014 | Hatakeyama | G03F 7/094 438/514 |
| 2014/0363958 A1 | 12/2014 | Hatakeyama et al. | |
| 2015/0030980 A1 | 1/2015 | Echigo et al. | |
| 2015/0037735 A1 | 2/2015 | Yang | |
| 2015/0090691 A1* | 4/2015 | Echigo | C07D 311/96 216/49 |
| 2015/0309403 A1* | 10/2015 | Rahman | G03F 7/091 430/5 |
| 2015/0368224 A1 | 12/2015 | Echigo | |
| 2015/0376157 A1 | 12/2015 | Echigo | |
| 2015/0376158 A1 | 12/2015 | Echigo | |
| 2015/0376202 A1 | 12/2015 | Echigo | |
| 2016/0130243 A1 | 5/2016 | Satou et al. | |
| 2016/0145231 A1 | 5/2016 | Echigo | |
| 2017/0183279 A1 | 6/2017 | Echigo | |
| 2017/0349564 A1 | 12/2017 | Toida | |
| 2018/0074402 A1 | 3/2018 | Toida et al. | |
| 2018/0074406 A1 | 3/2018 | Toida et al. | |
| 2018/0208703 A1* | 7/2018 | Okada | C08G 8/36 |
| 2018/0246409 A1* | 8/2018 | Toida | G03F 7/38 |

FOREIGN PATENT DOCUMENTS

| | | | |
|---|---|---|---|
| CN | 101889247 A | 11/2010 | |
| CN | 102070595 | 5/2011 | |
| CN | 103733136 A | 4/2014 | |
| CN | 103804196 A | 5/2014 | |
| CN | 104557552 A | 4/2015 | |
| EP | 1275673 | 1/2003 | |
| EP | 1300403 | 4/2003 | |
| EP | 1666970 * | 6/2006 | G03F 7/039 |
| EP | 2743249 | 6/2014 | |
| EP | 2743769 | 6/2014 | |
| EP | 2743770 A1 | 6/2014 | |
| EP | 3279190 A1 | 2/2018 | |
| JP | S48049508 A | 7/1973 | |
| JP | 62-094841 * | 5/1987 | G03C 1/72 |
| JP | S62191850 A | 8/1987 | |
| JP | H01283280 | 11/1989 | |
| JP | H04217675 | 8/1992 | |
| JP | H05034913 A | 2/1993 | |
| JP | H05134415 A | 5/1993 | |
| JP | H05163290 A | 6/1993 | |
| JP | 05-216235 * | 8/1993 | G03F 7/039 |
| JP | H06049402 A | 2/1994 | |
| JP | H06242607 A | 9/1994 | |
| JP | H07215833 | 8/1995 | |
| JP | H1025220 | 1/1998 | |
| JP | H10045764 A | 2/1998 | |
| JP | H11072925 | 3/1999 | |
| JP | 2001042525 | 2/2001 | |
| JP | 2002214769 | 7/2002 | |
| JP | 2002-334869 A | 11/2002 | |
| JP | 2002334896 | 11/2002 | |
| JP | 2002341542 | 11/2002 | |
| JP | 2003-201333 A | 7/2003 | |
| JP | 2004-177668 A | 6/2004 | |
| JP | 2004-271838 A | 9/2004 | |
| JP | 2005-250434 A | 9/2005 | |
| JP | 2005266741 A | 9/2005 | |
| JP | 2005326838 A | 11/2005 | |
| JP | 2005326868 A | 11/2005 | |
| JP | 2005346024 A | 12/2005 | |
| JP | 2006036648 | 2/2006 | |
| JP | 2006098869 | 4/2006 | |
| JP | 2006113136 | 4/2006 | |
| JP | 2006160663 | 6/2006 | |
| JP | 2006213634 | 8/2006 | |
| JP | 2006-259482 * | 9/2006 | G03F 7/11 |
| JP | 2006-259482 A | 9/2006 | |
| JP | 2007019294 | 1/2007 | |
| JP | 2007-199653 * | 8/2007 | G03F 7/11 |
| JP | 2007-226170 A | 9/2007 | |
| JP | 2007-226204 A | 9/2007 | |
| JP | 2007262398 | 10/2007 | |
| JP | 2007326847 | 12/2007 | |
| JP | 2008065081 | 3/2008 | |
| JP | 2008145539 A | 6/2008 | |
| JP | 2008-201954 A | 9/2008 | |
| JP | 2008239868 | 10/2008 | |
| JP | 2009073738 A | 4/2009 | |
| JP | 2009098155 A | 5/2009 | |
| JP | 2009108313 | 5/2009 | |
| JP | 2009155256 | 7/2009 | |
| JP | 2009173623 A | 8/2009 | |
| JP | 2009300978 | 12/2009 | |
| JP | 2010-160189 A | 7/2010 | |
| JP | 2010170013 | 8/2010 | |
| JP | 2010219295 | 9/2010 | |
| JP | 2010235643 | 10/2010 | |
| JP | 2011068624 | 4/2011 | |
| JP | 2011105887 | 6/2011 | |
| JP | 2011150023 | 8/2011 | |
| JP | 20121687 | 1/2012 | |
| JP | 2012-068652 * | 4/2012 | G03F 7/027 |
| JP | 2012-077295 A | 4/2012 | |
| JP | 2012083731 A | 4/2012 | |
| JP | 2012145897 | 8/2012 | |
| JP | 2013064978 A | 4/2013 | |
| JP | 2013-083833 A | 5/2013 | |

(56) References Cited

FOREIGN PATENT DOCUMENTS

| | | |
|---|---|---|
| JP | 2013-087173 A | 5/2013 |
| JP | 2013-137524 A | 7/2013 |
| JP | 2013-253161 A | 12/2013 |
| JP | 2014-196288 A | 10/2014 |
| JP | 2014205746 | 10/2014 |
| JP | 2015-018220 A | 1/2015 |
| JP | 2015-018221 A | 1/2015 |
| JP | 2015-018223 A | 1/2015 |
| JP | 2015087115 A | 5/2015 |
| JP | 2015514691 A | 5/2015 |
| KR | 10-2010-0095563 A | 8/2010 |
| WO | 9736960 | 10/1997 |
| WO | 0214434 | 2/2002 |
| WO | 03017002 | 2/2003 |
| WO | 2004/066377 A | 8/2004 |
| WO | 2005029189 A1 | 3/2005 |
| WO | 2005111724 | 11/2005 |
| WO | 2006068267 A1 | 6/2006 |
| WO | 2007-097457 * | 8/2007 ............... G03F 7/11 |
| WO | 2008053974 A1 | 5/2008 |
| WO | 2008137816 A2 | 11/2008 |
| WO | 2009/072465 A | 6/2009 |
| WO | 2009119201 A1 | 10/2009 |
| WO | 2009145224 | 12/2009 |
| WO | 2011/034062 A | 3/2011 |
| WO | 2012165507 A1 | 12/2012 |
| WO | 2013/010102 A2 | 1/2013 |
| WO | 2013/024779 * | 2/2013 ............... G03F 7/11 |
| WO | 2013024777 A1 | 2/2013 |
| WO | 2013024778 A1 | 2/2013 |
| WO | 2013066067 | 5/2013 |
| WO | 2013184755 | 12/2013 |
| WO | 2014/050690 * | 4/2014 ............... G02B 1/04 |
| WO | 2014123032 A1 | 8/2014 |
| WO | 2014/199660 | 12/2014 |

OTHER PUBLICATIONS

Protiva et al., "Potential metabolites or tricyclic neuroleptics" 3,7-dimethoxy and 7,8-dimethoxy derivatives of 10-(4-methylpiperazino)-10,11-dihydrodibenzo[b,f]thiepin, Coll. Czech. Chem. Commun. vol. 46 (1981) pp. 1808-1817.*

Protiva et al., "Potential metabolites of tricyclic neuroleptics: 2,8-dihydroxy and 3,8-dihydroxy derivatives of 10-(4-methylpiperazino)-10,1 1-dihydrodibenzo(b,l)thiepin", Coll. Check. Chem. Commun, vol. 44 pp. 2987-2996 (1979).*

Clowes "Studies of the Scholl reaction: oxidative dehydrogenation involving 1-ethoxynaphthylenen and related compounds", J Chem. Soc (C) 2519-2526 (1968).*

Cameron et al., "Synthesis of a natural polychloro dinaphthofuran quinone", Tetrahed. Lett., vol. 21(14) pp. 1385-1386 (1980).*

Percec et al., "Synthesis of aromatic polyethers by Scholl reaction. VI aromatic polyethers by cation-radical polymerization of 4,4'- . . . ", Macromol., vol. 25(1) pp. 64-74 (1992).*

Percec et al., "Synthesis of aromatic polyethers by Scholl reaction. I poly(1,1'dinaphthyl ether phenyl sulfone) . . . ", J polymer. Sci., Pt A, Polym. Chem., vol. 26 pp. 783-805 (1988).*

Areephopng et al., "A concise synthesis of functionalized 7-oxa-[5-helicenes", Tetrahed. Lett., vol. 45 pp. 3067-3070 (2004).*

Bentley, K.W. et al., Tetrahedron Letter 1959, vol. 1 Issue 2, pp. 11-14.

Dann, von Otto et al., Justus Liebigs Annalen Der Chemie, 1963, vol. 667, Issue 1, pp. 116-125.

Chatterjea, J.N., Journal of the Indian Chemical Society, 1957, vol. 34, Issue 4,pp. 299-305 (2).

International Search Report dated Feb. 9, 2016, for PCT/JP2015/084907 and English translation of the same (7 pages).

International Search Report for PCT/JP2014/051775 dated Feb. 25, 2014 and English translation (4 pages).

Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.

Brecher, Jonathan, Graphical Representation Standards for Chemical Structure Diagrams, Pure Appl. Chem., 2008, pp. 277-410, vol. 80, No. 2, Cambridge, Massachusetts.

English Translation of JP H01-283280 A, Nov. 14, 1989.

Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.

International Search Report dated Feb. 25, 2014 for PCT/JP2012/051775 and English translation of the same (4 pages).

International Search Report dated Mar. 25, 2014 for International Application No. PCT/JP2014/052524 with English Translation (8 pages).

International Search Report dated May 13, 2014 for International Application No. PCT/JP2014/052530 with English Translation (8 pages).

International Search Report dated Oct. 23, 2012 issued in International Application No. PCT/JP2012/070304.

International Search Report dated Sep. 11, 2012 for International Application No. PCT/JP2012/070305 with English Translation (5 pages).

International Search Report on Patentability for PCT/JP2016/056332 dated May 31, 2016; English translation submitted herewith (11 pages).

International Search Report on Patentability for PCT/JP2016/056333 dated May 24, 2016; English translation submitted herewith (7 pages).

Jha Amitabh and Beal Jennifer, "Convenient synthesis of 12H-benzo[a]xanthenes from 2-tetralone," Tetrahedron Letters, 2004, vol. 45, No. 49, pp. 8999-9001.

Journal of the Chemical Society, p. 5336-5341 (Nov. 1963).

Machine English Translation of JP 2008-239868 A, Oct. 9, 2008.

Nakayama, Tomonari, Nomura, Masayoshi, Haga, Kohji, and Ueda, Mitsuru, A New Three-Component Photoresist Based on Calix[4]resorcinarene Derivative, a Cross-Linker, and a Photo-acid Generator, The Chemical Society of Japan, Bulletin of the Chemical Society of Japan, 1998, vol. 71, No. 12, pp. 2979-2984.

Nature, 161:930-931 (1948).

Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.

Ohishi Takeshi. Tetrahedron Letters 42 (2001) 2493-2496.

Shinji Okazaki et al., "New Trends of Photoresists", CMC Publishing Co., Ltd., Sep. 2009, p. 211-259.

Osman A-M, Reactions Between Chloro-p-benzoquinones and Beta-Naphtol, Journal of Organic Chemistry, 1957, vol. 22, pp. 342-344.

Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.

Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.

Sirringhaus Henning et al., Dibenzothienobisbenzothiophene—a novel fused-ring oligomer with high field-effect mobility, Journal of Materials Chemistry, 1999, vol. 9, pp. 2095-2101.

Tian-jun Liu, Ke-shen Zhang, Yong-jun Chen, Dong Wang and Chao-jun Li, "Chiral Conjugated Oligomer Based on 1, 1'-Binol With 3, 3 '-Acetylene-Phenylene-Acetylene Spacer", Chinese Journal of Polymer Science, Mar. 8, 2001, vol. 19, No. 5, p. 521-526.

Written Opinion of the International Searching Authority issued in International Application No. PCT/JP2012/070304 (including translation), dated Oct. 23, 2012.

Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.

Burnett, James C., et al. "Novel small molecule inhibitors of botulinum neurotoxin A metalloprotease activity," Biochemical and Biophysical Research Communications, vol. 310, No. 1, Oct. 2003, pp. 84-93.

(56) References Cited

OTHER PUBLICATIONS

European Journal of Medicinal Chemistry, published bi-monthly, Ejmcs, 13(4): 381-385 (1978).
Skandinavisches Archiv fuer Physiologie, 43: 215-243 (1923).
International Preliminary Report on Patentability issued in International Application No. PCT/JP2012/070304.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
Luo, Junfei et al., "Salicylic acids as readily available statring materials for the synthesis of meta-substitutes biaryls," ChemComm, 2015, vol. 51, pp. 3127-3130.

\* cited by examiner

COMPOUND, RESIN, MATERIAL FOR FORMING UNDERLAYER FILM FOR LITHOGRAPHY, UNDERLAYER FILM FOR LITHOGRAPHY, PATTERN FORMING METHOD, AND PURIFICATION METHOD

CROSS-REFERENCE TO RELATED APPLICATIONS

This application is a U.S. national phase application filed under 35 U.S.C. § 371 of International Application PCT/JP 2015/084907, filed on Dec. 14, 2015, designating the United States, which claims priority from Japanese Application Number 2014-262564, filed Dec. 25, 2014, which are hereby incorporated herein by reference in their entirety.

FIELD OF THE INVENTION

The present invention relates to a compound, a resin, a material for forming an underlayer film for lithography, an underlayer film for lithography, a pattern forming method, and a purification method.

BACKGROUND OF THE INVENTION

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. If the resist film is merely made thinner in response to such a demand, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As the material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, examples can include a resist underlayer film for lithography, having a smaller selection ratio of dry etching rate than the resist. As the material for forming such a resist underlayer film for lithography, there has been proposed a resist underlayer film material including a polymer having a specific repeating unit (see, for example, Patent Literature 2). Furthermore, examples can include a resist underlayer film for lithography, having a smaller selection ratio of dry etching rate than the semiconductor substrate. As the material for forming such a resist underlayer film for lithography, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specific constituent unit, and an organic solvent (see, for example, Patent Literatures 4 and 5).

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but one is demanded which not only has such a high solvent solubility as to be able to be applied to a wet process such as a spin coating method or screen printing, but also simultaneously satisfies heat resistance and etching resistance at a high level and is further improved in solubility in a safe solvent for high stabilization of product quality.

The present invention has been made in view of the above problem, and an object thereof is to provide a compound and a resin, a material for forming an underlayer film, and a pattern forming method, which are useful for forming a photoresist underlayer film, which can be applied to a wet process, which are excellent in heat resistance and etching resistance, and which are further improved in solubility in a safe solvent.

The present inventors have intensively studied to solve the above problem, and as a result, have found that the above problem can be solved by using a compound or a resin having a specific structure, thereby leading to the completion of the present invention.

That is, the present invention provides the following [1] to [19].

[1]

A compound represented by the following formula (1):

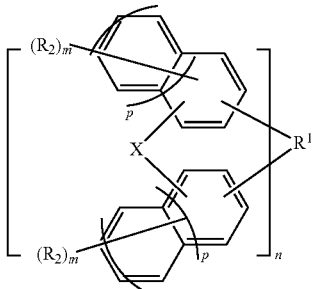

(1)

wherein each X independently represents an oxygen atom or a sulfur atom, or non-crosslinking, $R^1$ represents a single bond or a 2n-valent group having 1 to 30 carbon atoms, the group may have an alicyclic hydrocarbon group, a double bond, a hetero atom, or an aryl group having 6 to 30 carbon atoms, each $R^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one $R^2$ represents an alkoxy group having 1 to 30 carbon atoms or an aryloxy group having 6 to 30 carbon atoms, each m is independently an integer of 1 to 6, each p is independently 0 or 1, and n is an integer of 1 to 4.

[2]

The compound according to [1], wherein the compound represented by the formula (1) is a compound represented by the following formula (1A-2):

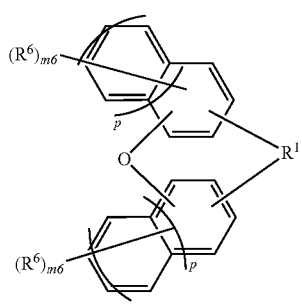

(1A-2)

wherein $R^1$ and p are the same as those described above, $R^6$ is the same as $R^2$ defined in the formula (1), and each $m^6$ is independently an integer of 1 to 3.

[3]

The compound according to [1], wherein the compound represented by the formula (1) is a compound represented by the following formula (1B-2):

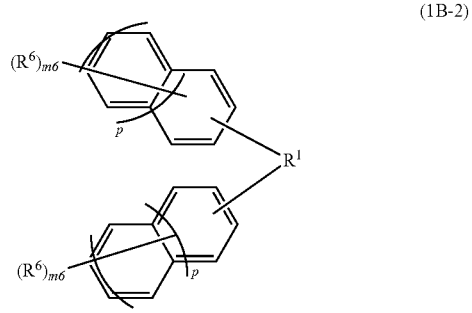

(1B-2)

wherein $R^1$ and p are the same as those described above, $R^6$ is the same as $R^2$ defined in the formula (1), and each $m^6$ is independently an integer of 1 to 3.

[4]

The compound according to [2], wherein the compound represented by the formula (1A-2) is a compound represented by the following formula (BisN-1-CH1) or the following formula (BisN-1-CH2).

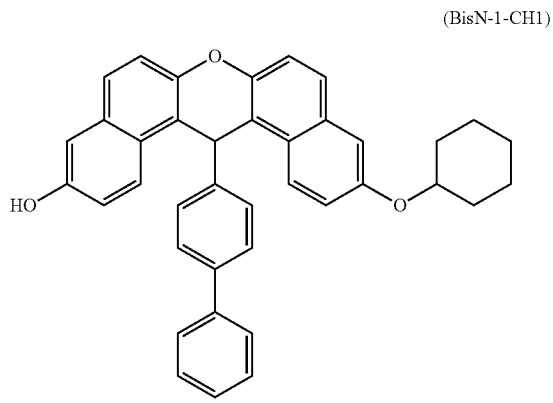

(BisN-1-CH1)

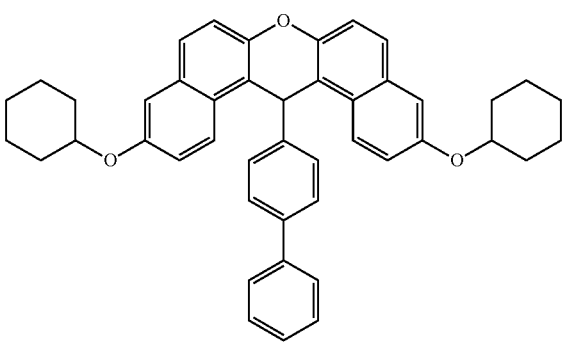

(BisN-1-CH2)

[5]

The compound according to [2], wherein the compound represented by the formula (1A-2) is a compound represented by the following formula (BisN-1-PH1) or the following formula (BisN-1-PH2).

(BisN-1-PH1)

(BisN-1-PH2)

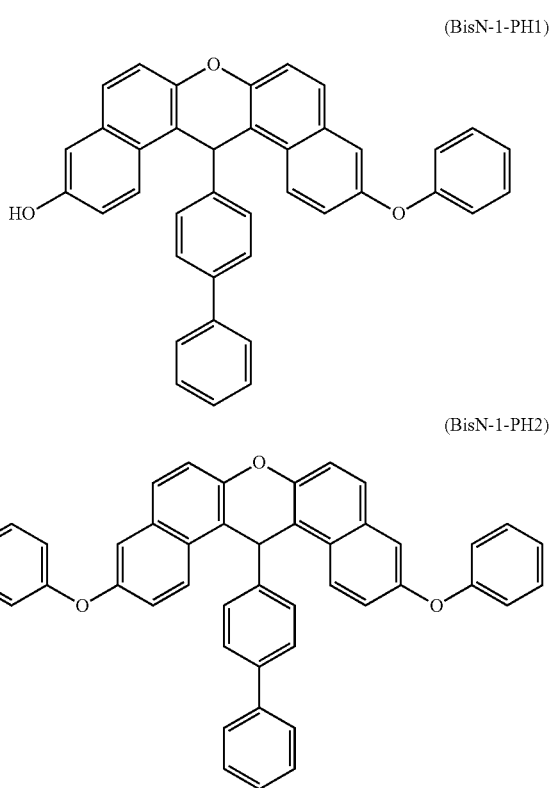

[6]

A resin obtained with the compound according to any one of [1] to [5] as a monomer.

[7]

The resin according to [6], which is obtained by a reaction of the compound according to any one of [1] to [5] with a compound having crosslinking reactivity.

[8]

The resin according to [7], wherein the compound having crosslinking reactivity is at least one selected from the group consisting of aldehyde, ketone, carboxylic acid, carboxylic halide, a halogen-containing compound, an amino compound, an imino compound, isocyanate and an unsaturated hydrocarbon group-containing compound.

[9]

The resin according to [6], comprising a structure represented by the following formula (2):

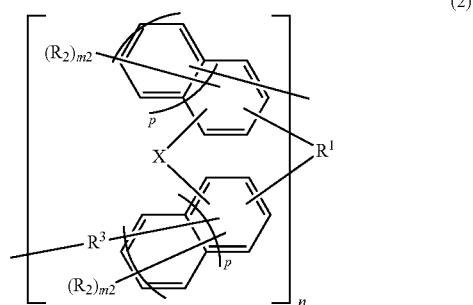

(2)

wherein each X independently represents an oxygen atom or a sulfur atom, or non-crosslinking, $R^1$ represents a single bond or a 2n-valent group having 1 to 30 carbon atoms, the group may have an alicyclic hydrocarbon group, a double bond, a hetero atom, or an aryl group having 6 to 30 carbon atoms, each $R^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one $R^2$ represents an alkoxy group having 1 to 30 carbon atoms or an aryloxy group having 6 to 30 carbon atoms, each $R^3$ independently represents a single bond, or a straight or branched alkylene group having 1 to 20 carbon atoms, each $m^2$ is independently an integer of 1 to 5, p is independently 0 or 1, and n is an integer of 1 to 4.

[10]

The resin according to [9], wherein the resin having the structure represented by the formula (2) is a resin having a structure represented by the following formula (2A):

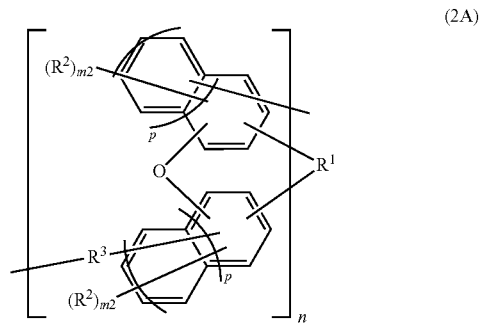

(2A)

wherein $R^1$, $R^2$, $R^3$, $m^2$, p and n are the same as those described above.

[11]

The resin according to [9], wherein the resin having the structure represented by the formula (2) is a resin having a structure represented by the following formula (2B):

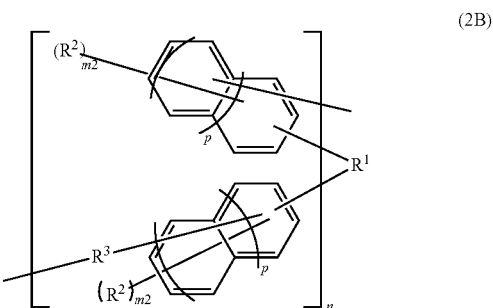

(2B)

wherein $R^1$, $R^2$, $R^3$, $m^2$, p and n are the same as those described above.

[12]

A material for forming an underlayer film for lithography, comprising the compound according to any one of [1] to [5] and/or the resin according to any one of [6] to [11].

[13]

The material for forming the underlayer film for lithography according to [12], further comprising an organic solvent.

[14]

The material for forming the underlayer film for lithography according to [12] or [13], further comprising an acid generating agent.

[15]

The material for forming the underlayer film for lithography according to any one of [12] to [14], further comprising a crosslinking agent.

[16]

An underlayer film for lithography, formed from the material for forming the underlayer film for lithography according to any one of [12] to [15].

[17]

A resist pattern forming method, comprising step (A-1) of forming an underlayer film on a substrate by using the material for forming the underlayer film for lithography according to any one of [12] to [15], step (A-2) of forming at least one photoresist layer on the underlayer film, and step (A-3) of, after step (A-2), irradiating a predetermined region of the photoresist layer with radiation, followed by developing.

[18]

A circuit pattern forming method, comprising step (B-1) of forming an underlayer film on a substrate by using the material for forming the underlayer film for lithography according to any one of [12] to [15], step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

[19]

A purification method, comprising a step of bringing a solution (A) comprising an organic solvent optionally immiscible with water, and the compound according to any one of [1] to [5] or the resin according to any one of [6] to [11] into contact with an acidic aqueous solution for extraction.

According to the present invention, it is possible to provide a compound, a resin, and a material for forming an underlayer film for lithography, which are useful for forming a photoresist underlayer film, which can be applied to a wet process, which are excellent in heat resistance and etching resistance, and which are further improved in solubility in a safe solvent.

DESCRIPTION OF EMBODIMENTS

Hereinafter, an embodiment (hereinafter, referred to as the present embodiment) of the present invention will be described. It is to be noted that the present embodiments are illustrative for describing the present invention, and the present invention is not limited only to the present embodiments.

[Compound]

A compound of the present embodiment is represented by the following formula (1).

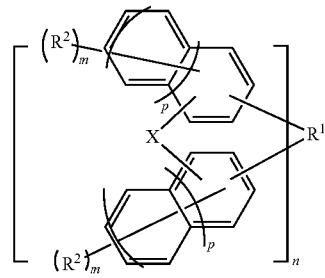

(in formula (1), each X independently represents an oxygen atom or a sulfur atom, or non-crosslinking, $R^1$ represents a single bond or a 2n-valent group having 1 to 30 carbon atoms, the group may have an alicyclic hydrocarbon group, a double bond, a hetero atom, or an aryl group having 6 to 30 carbon atoms, each $R^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one $R^2$ represents an alkoxy group having 1 to 30 carbon atoms or an aryloxy group having 6 to 30 carbon atoms, each m is independently an integer of 1 to 6, each p is independently 0 or 1, and n is an integer of 1 to 4.)

The compound of the present embodiment has the above structure, and therefore is useful for forming a photoresist underlayer film, can be applied to a wet process, is excellent in heat resistance and etching resistance, and is further improved in solubility in a safe solvent. The compound of the present embodiment can be evaluated to have a high heat resistance, a relatively high carbon concentration, a relatively low oxygen concentration, and also a high solvent solubility, in view of structural characteristics. When such a compound having a predetermined structure is used for a material for forming an underlayer film for lithography, an underlayer film, whose degradation is suppressed at high-temperature baking and which is also excellent in etching resistance to oxygen plasma etching or the like, can be formed, and furthermore, the compound is also excellent in adhesiveness with a resist layer and therefore can provide an excellent resist pattern.

In the formula (1), each X independently represents an oxygen atom or a sulfur atom, or non-crosslinking. Here, the case where X represents non-crosslinking means that the compound represented by the formula (1) is a compound represented by the following formula (1B).

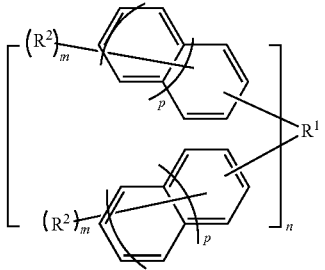

(in formula (1B), $R^1$, $R^2$, m, p and n are the same as those described above.)

$R^1$ represents a single bond or a 2n-valent group having 1 to 30 carbon atoms. The compound of the present embodiment has a structure in which respective benzene rings are bonded to each other via $R^1$. Herein, the 2n-valent group may have an alicyclic hydrocarbon group, a double bond, a hetero atom, or an aryl group having 6 to 30 carbon atoms.

Each $R^2$ independently represents a monovalent group selected from the group consisting of a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms and a hydroxyl group, and m of $R^2$(s) are bonded to each aromatic ring. Herein, at least one $R^2$ represents an alkoxy group having 1 to 30 carbon atoms or an aryloxy group having 6 to 30 carbon atoms.

In addition, each m is independently an integer of 1 to 6. Each p is independently 0 or 1. n is an integer of 1 to 4.

Herein, the 2n-valent group represents an alkylene group having 1 to 30 carbon atoms when n=1, an alkanetetrayl group having 1 to 30 carbon atoms when n=2, an alkanehexayl group having 2 to 30 carbon atoms when n=3, and an alkaneoctayl group having 3 to 30 carbon atoms when n=4. Examples of the 2n-valent group include those having a straight, branched or cyclic structure.

The 2n-valent group may also have an alicyclic hydrocarbon group, a double bond, a hetero atom, or an aryl group having 6 to 30 carbon atoms. Herein, the alicyclic hydrocarbon group also includes a bridged alicyclic hydrocarbon group.

Furthermore, the alkoxy group having 1 to 30 carbon atoms means a group configured from a group selected from a straight hydrocarbon group, a branched hydrocarbon group, an alicyclic hydrocarbon group, an aromatic hydrocarbon group and a group including a combination of two or more thereof, as well as an oxygen atom. Herein, the alicyclic hydrocarbon group also includes a bridged alicyclic hydrocarbon group. The alkoxy group may also have a double bond, a hetero atom, or a halogen atom.

The alkoxy group having 1 to 30 carbon atoms is not particularly limited, but preferable examples thereof include a methoxy group, an ethoxy group, a propoxy group, a butoxy group, a pentyloxy group, a hexyloxy group, a cyclobutyloxy group, a cyclopentyloxy group, a cyclohexyloxy group, a cyclohexenyloxy group, an isophoronyloxy group, a norbornanyloxy group, an adamantyloxy group, a tricyclodecanyloxy group, a pyridinyloxy group, a phenyloxy group, a methylphenyloxy group, a dimethylphenyloxy group, an ethylphenyloxy group, a fluorophenyloxy group, a chlorophenyloxy group, a bromophenyloxy group, an iodophenyloxy group, a hydroxyphenyloxy group, a methoxyphenyloxy group, an aminophenyloxy group, a nitrophenyloxy group, a cyanophenyloxy group, a phenylphenyloxy group, a phenyloxyphenyloxy group, a naphthyloxy group, a methylnaphthyloxy group, a dimethylnaphthyloxy group, an ethylnaphthyloxy group, a fluoronaphthyloxy group, a chloronaphthyloxy group, a bromonaphthyloxy group, an iodonaphthyloxy group, a hydroxynaphthyloxy group, a methoxynaphthyloxy group, an aminonaphthyloxy group, a nitronaphthyloxy group, a cyanonaphthyloxy group, a phenylnaphthyloxy group, a phenyloxynaphthyloxy group, an anthracenyloxy group, a pyrenyloxy group and a fluorenyloxy group, more preferably includes a cyclobutyloxy group, a cyclopentyloxy group, a cyclohexyloxy group, a cyclohexenyloxy group, an isophoronyloxy group, a norbornanyloxy group, an adamantyloxy group, a tricyclodecanyloxy group, a pyridinyloxy group, a phenyloxy group, a methylphenyloxy group, a dimethylphenyloxy group, an ethylphenyloxy group, a fluorophenyloxy group, a chlorophenyloxy group, a bromophenyloxy group, an iodophenyloxy group, a hydroxyphenyloxy group, a methoxyphenyloxy group, an aminophenyloxy group, a nitrophenyloxy group, a cyanophenyloxy group, a phenylphenyloxy group, a phenyloxyphenyloxy group, a naphthyloxy group, a methylnaphthyloxy group, a dimethylnaphthyloxy group, an ethylnaphthyloxy group, a fluoronaphthyloxy group, a chloronaphthyloxy group, a bromonaphthyloxy group, an iodonaphthyloxy group, a hydroxynaphthyloxy group, a methoxynaphthyloxy group, an aminonaphthyloxy group, a nitronaphthyloxy group, a cyanonaphthyloxy group, a phenylnaphthyloxy group, a phenyloxynaphthyloxy group, an anthracenyloxy group, a pyrenyloxy group and a fluorenyloxy group, further preferably includes a cyclobutyloxy group, a cyclopentyloxy group, a cyclohexyloxy group, a cyclohexenyloxy group, an isophoronyloxy group, a norbornanyloxy group, an adamantyloxy group, a tricyclodecanyloxy group, a pyridinyloxy group, a phenyloxy group, a methylphenyloxy group, a dimethylphenyloxy group, an ethylphenyloxy group, a methoxyphenyloxy group, a phenylphenyloxy group, a phenyloxyphenyloxy group, a naphthyloxy group, a methylnaphthyloxy group, a dimethylnaphthyloxy group, an ethylnaphthyloxy group, a methoxynaphthyloxy group, a phenylnaphthyloxy group, a phenyloxynaphthyloxy group, an anthracenyloxy group, a pyrenyloxy group and a fluorenyloxy group, and particularly preferably includes a cyclohexyloxy group and a phenyloxy group.

The aryloxy group having 6 to 30 carbon atoms means a group configured from an aromatic hydrocarbon group having 6 to 30 carbon atoms, and an oxygen atom, and contributes to an enhancement in solubility of the compound represented by the formula (1). Specific examples of such an aryloxy group having 6 to 30 carbon atoms include, but not limited to the following, a phenyloxy group, a methylphenyloxy group, a dimethylphenyloxy group, a trimethylphenyloxy group, an ethylphenyloxy group, a propylphenyloxy group, a butylphenyloxy group, a cyclohexylphenyloxy group, a biphenyloxy group, a terphenyloxy group, a naphthyloxy group, a fluorenyloxy group, an anthracyloxy group, a pyrenyloxy group, a methylpyrenyloxy group and a dimethylpyrenyloxy group.

The compound represented by the formula (1) has a high heat resistance derived from rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. As a result, a material for forming an underlayer film for lithography using such a compound tends to be improved in terms of embedding properties and planarizing properties in a relatively advantageous manner. In addition, the compound has a relatively high carbon concentration to thereby impart also a high etching resistance. Furthermore, the compound having an alkoxy group having 1 to 30 carbon atoms can further improve solubility in a safe solvent for high stabilization of product quality.

Herein, the compound represented by the formula (1) is preferably a compound represented by the following formula (1A) from the viewpoint of an enhancement in heat resistance derived from rigid structure formation.

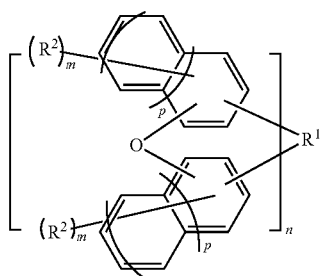
(1A)

In the formula (1A), $R^1$, $R^2$, m, p and n are the same as those described above.

In addition, the compound represented by the formula (1) is preferably a compound represented by the following formula (1B) from the viewpoint of an enhancement in solubility in a safe solvent.

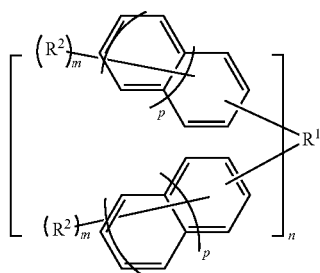
(1B)

In the formula (1B), $R^1$, $R^2$, m, p and n are the same as those described above.

The compound represented by the formula (1A) is more preferably a compound represented by formula (1A-1) from the viewpoint of an enhancement in heat resistance by an enhancement in the degree of crosslinking during baking, derived from $R^5O$ group introduction.

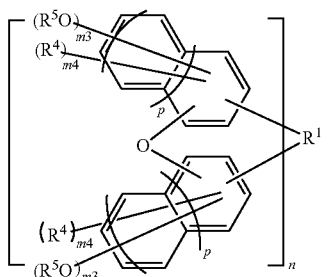
(1A-1)

(in formula (1A-1), each $R^4$ independently represents a straight, branched or cyclic alkyl group having 1 to 10 carbon atoms, an aryl group having 6 to 10 carbon atoms, an alkenyl group having 2 to 10 carbon atoms, or a hydroxyl group, and $R^5$ represents a monovalent group having 1 to 30 carbon atoms and also represents a group selected from monovalent groups including a straight hydrocarbon group, a branched hydrocarbon group, an alicyclic hydrocarbon group, an aromatic hydrocarbon group, and a combination of two or more thereof. The group may also have a double bond, a hetero atom, or a halogen atom. Herein, the alicyclic hydrocarbon group also includes a bridged alicyclic hydrocarbon group. Each $m_3$ is independently an integer of 0 to 4, in which at least one $m_3$ is 1, each $m_4$ is independently an integer of 0 to 3, $m_3+m_4$ is an integer of 1 to 4, and $R^1$, n and p are the same as those described above.)

The compound represented by the formula (1B) is more preferably a compound represented by formula (1B-1) from the viewpoint of a further enhancement in solubility in a safe solvent derived from $R^5O$ group introduction.

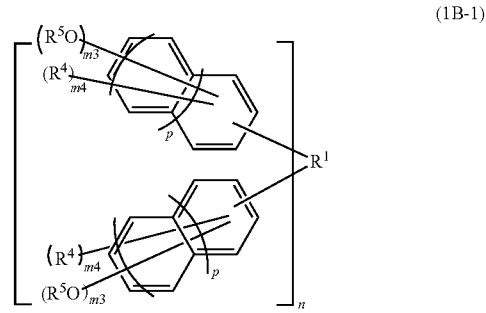
(1B-1)

(in formula (1B-1), $R^1$, $R^4$, $R^5$, $m^3$, $m^4$, n and p are the same as those described above.)

In addition, the compound represented by the formula (1) is preferably a mode where n=1 in the formula (1), namely, a compound represented by the following formula (1-2) from the viewpoint of having a low molecular weight.

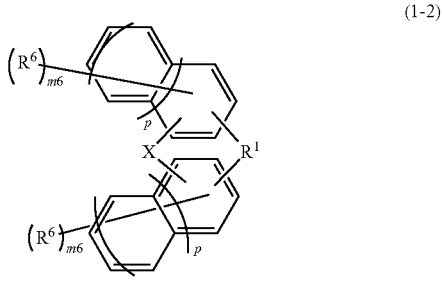
(1-2)

In the formula (1-2), X, $R^1$ and p are the same as defined in the formula (1), $R^6$ is the same as $R^2$ defined in the formula (1), and $m^6$ is an integer of 1 to 3.

The compound represented by the formula (1-2) is preferably a mode where X=O in the formula (1-2), namely, a compound represented by the following formula (1A-2) from the viewpoint of an enhancement in heat resistance derived from rigid structure formation.

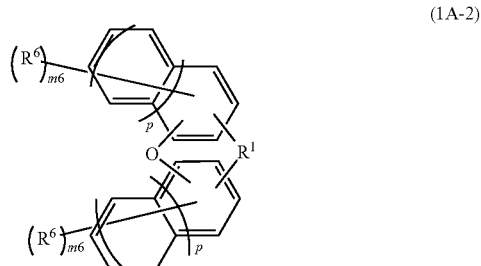
(1A-2)

In the formula (1A-2), $R^1$ and p are the same as defined the formula (1). $R^6$ is the same as $R^2$ defined in the formula (1), and $m^6$ is an integer of 1 to 3.

In addition, the compound represented by the formula (1-2) is more preferably a mode where X represents non-crosslinking in the formula (1-2), namely, a compound represented by the following formula (1B-2) from the viewpoint of an enhancement in solubility in a safe solvent.

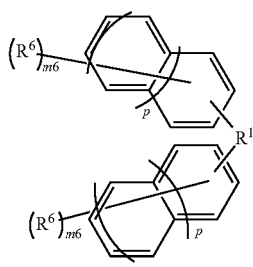
(1B-2)

In the formula (1B-2), $R^1$ and p are the same as defined in the formula (1). $R^6$ is the same as $R^2$ defined in the formula (1), and $m^6$ is an integer of 1 to 3.

The compound represented by the formula (1A-2) is preferably a compound represented by the following formula (1A-3) from the viewpoint that both of solubility and heat resistance are satisfied.

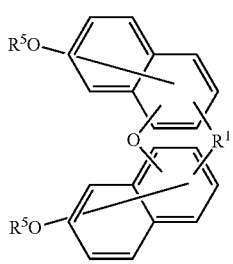
(1A-3)

In the formula (1A-3), $R^1$ is the same as defined in the formula (1), and $R^5$ is the same as defined in the formula (1A-1).

The compound represented by the formula (1B-2) is preferably a compound represented by the following formula (1B-3) from the viewpoint that both of solubility and heat resistance are satisfied.

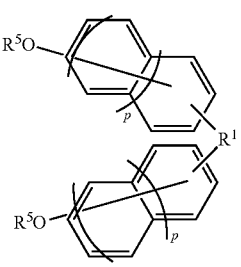
(1B-3)

In the formula (1B-3), $R^1$ is the same as defined in the formula (1), and $R^5$ is the same as defined in the formula (1A-1).

Specific examples of the compound represented by the formula (1) are shown below, but are not limited to those exemplified herein.

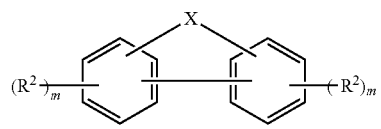

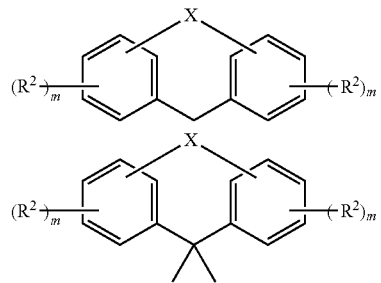

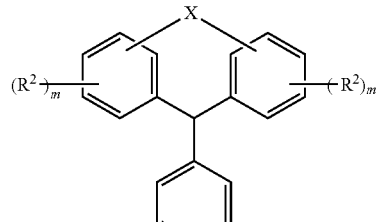

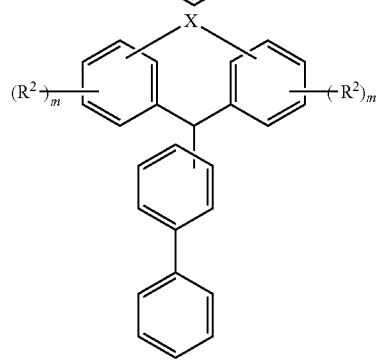

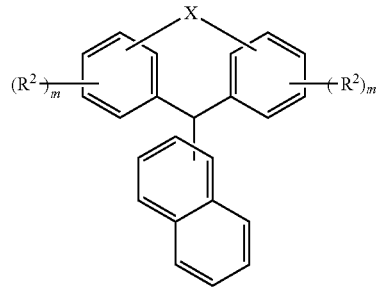

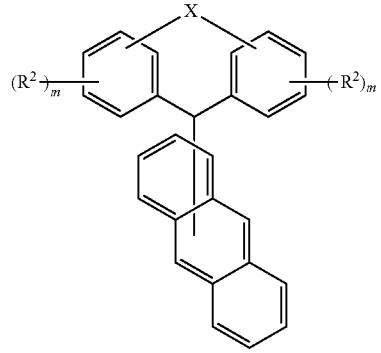

-continued
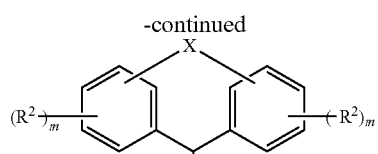
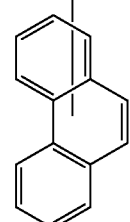
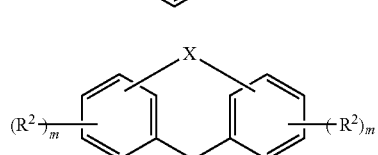
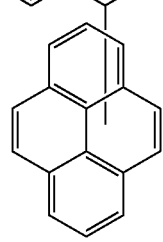
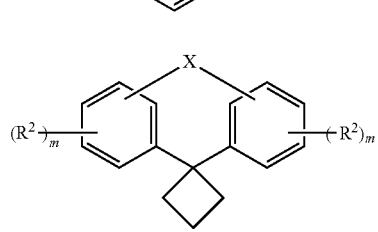
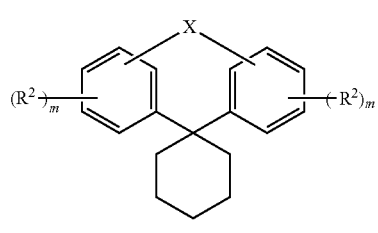
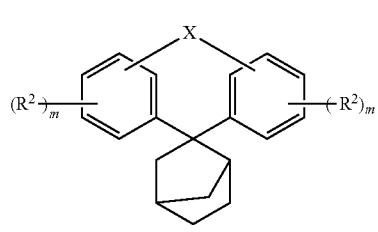
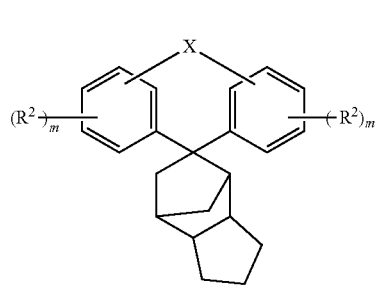
-continued
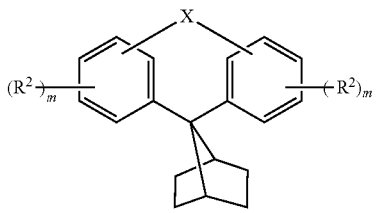
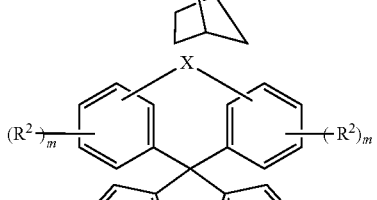
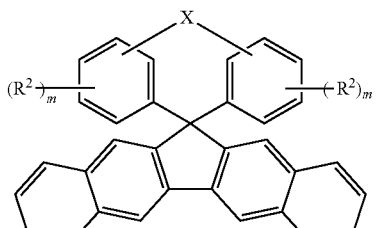
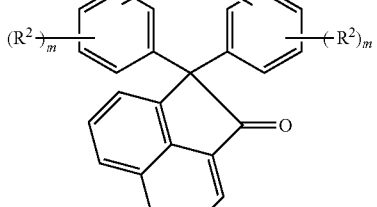
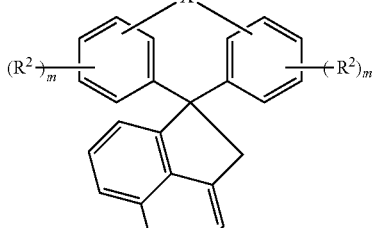
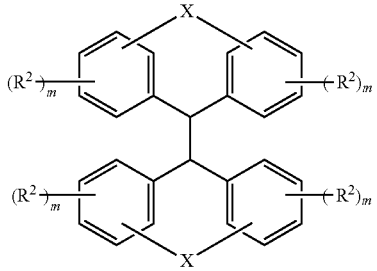

-continued
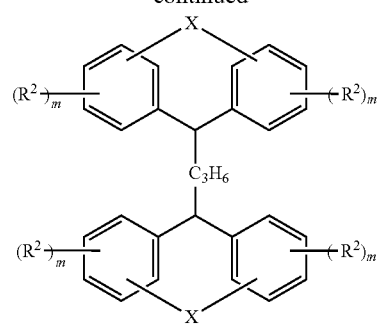
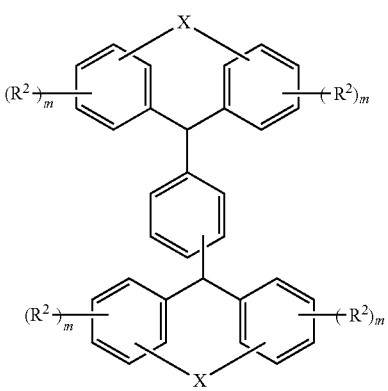
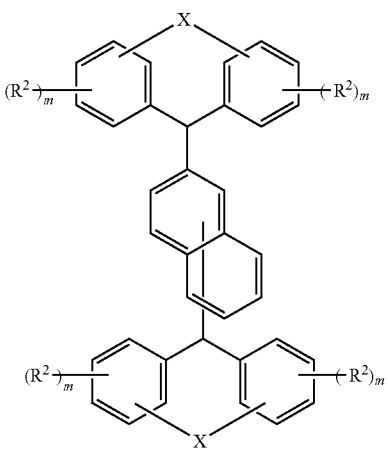
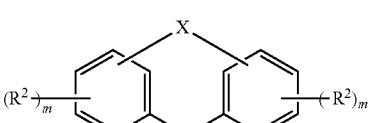
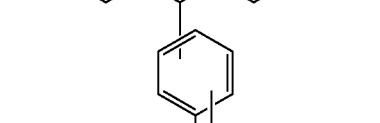
-continued
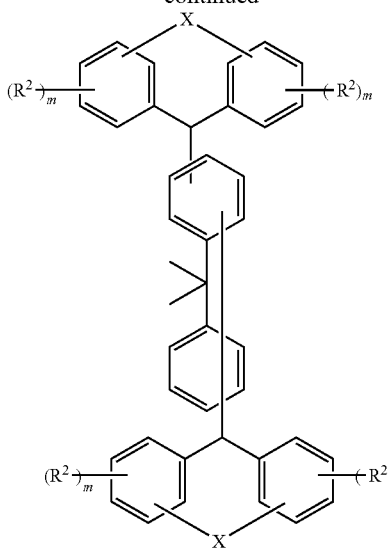
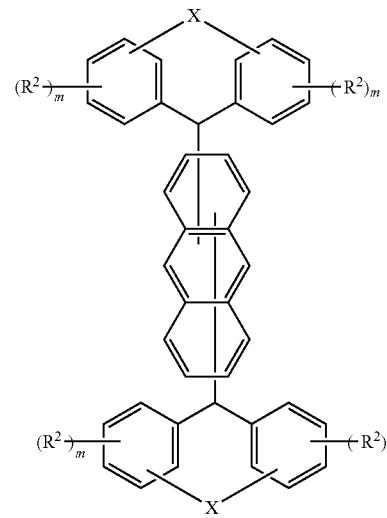
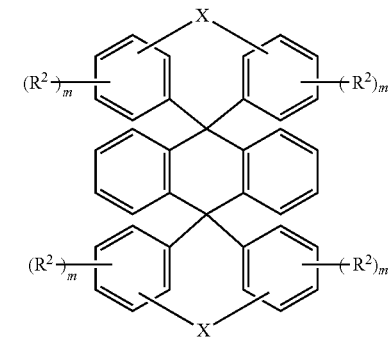

-continued
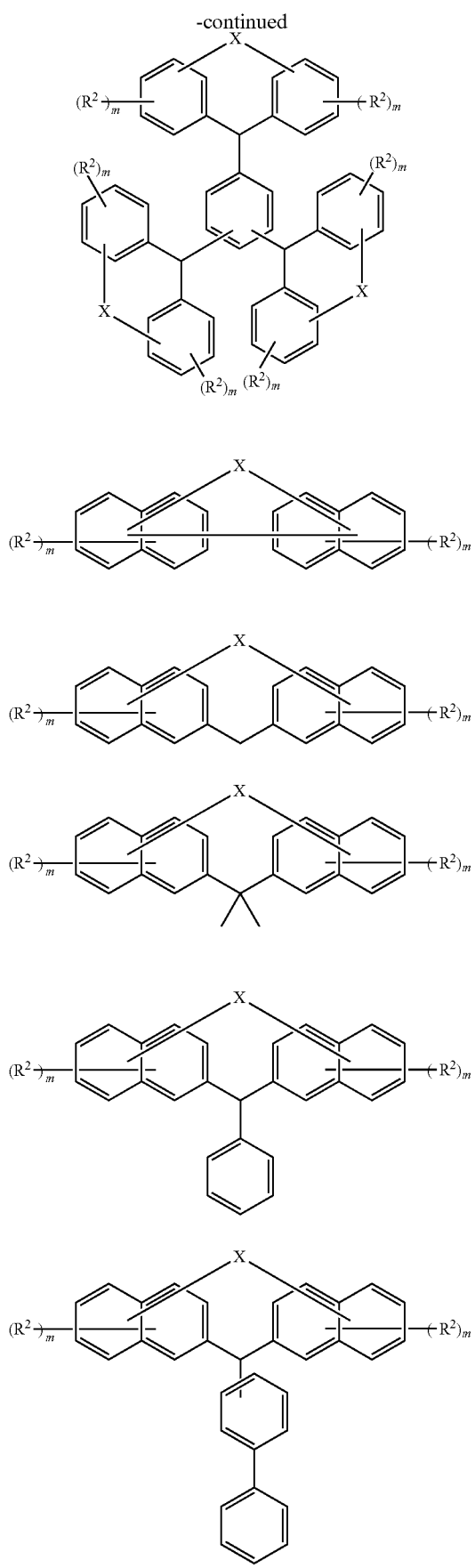
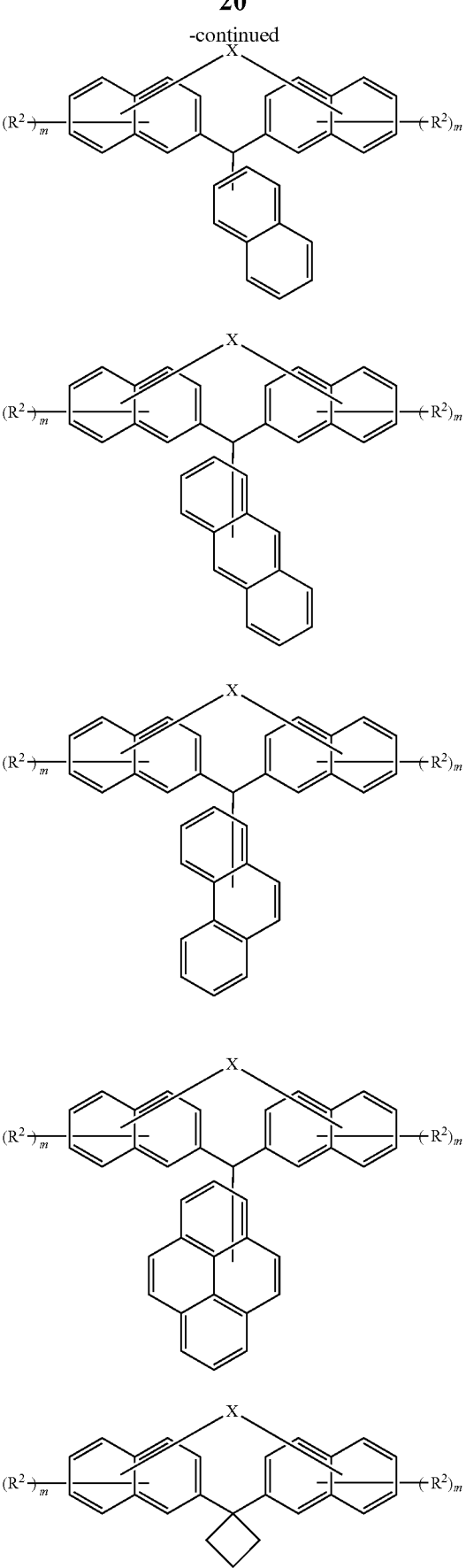

-continued
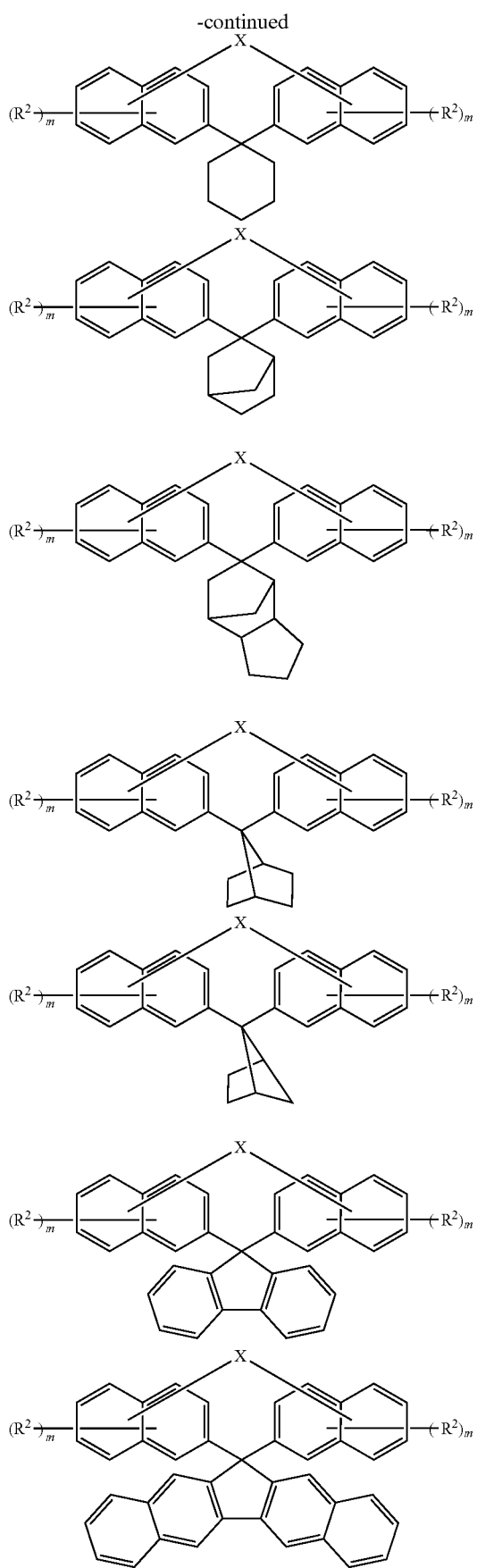
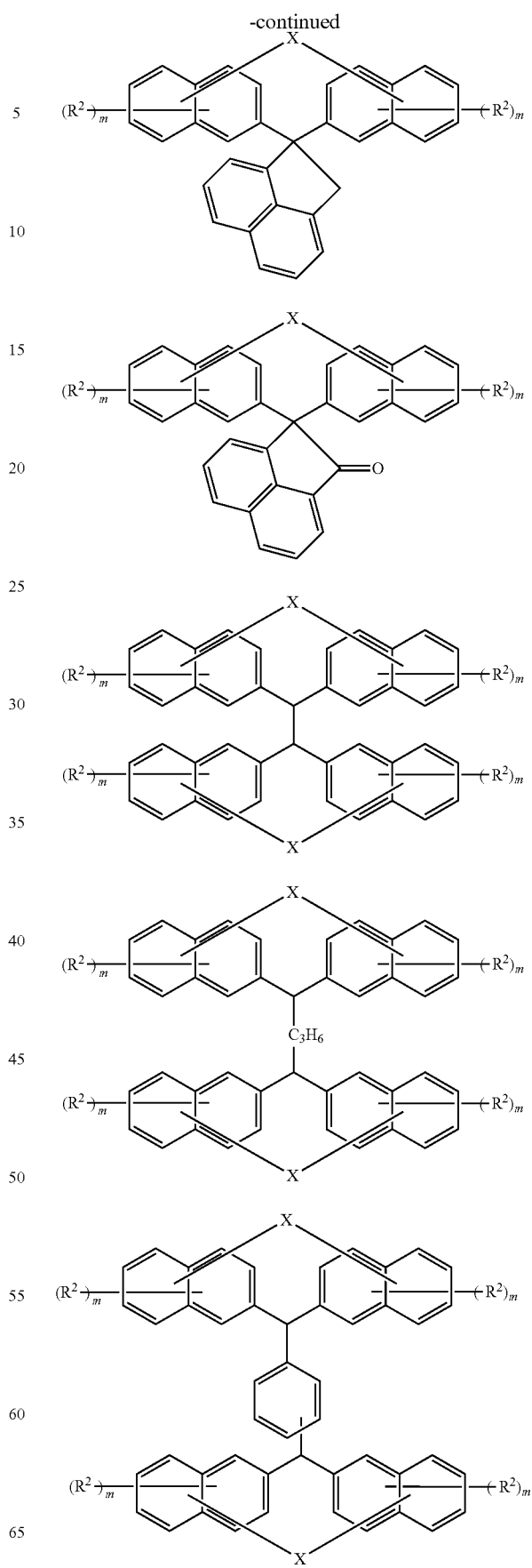

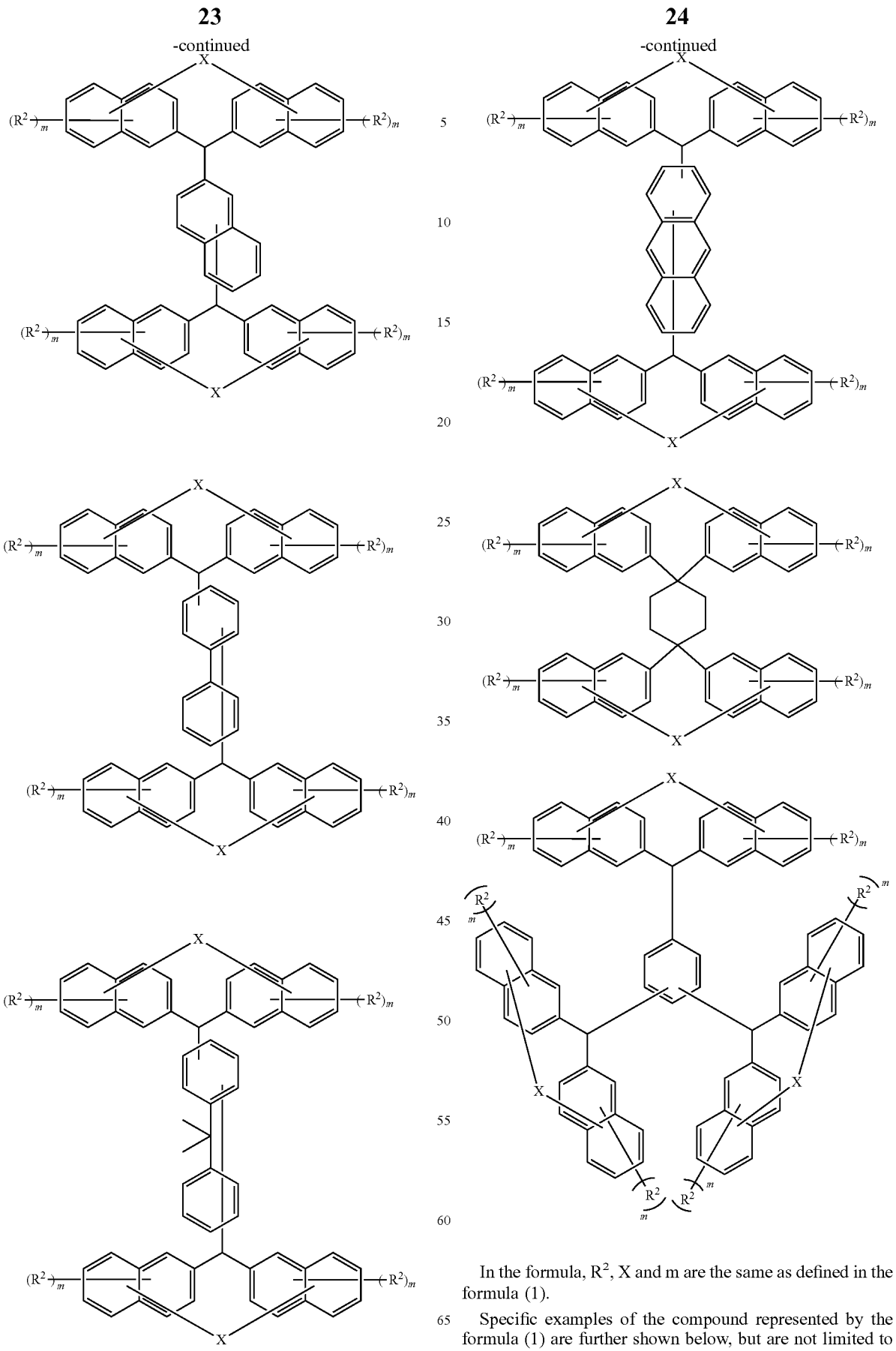
In the formula, $R^2$, X and m are the same as defined in the formula (1).
Specific examples of the compound represented by the formula (1) are further shown below, but are not limited to those exemplified herein.

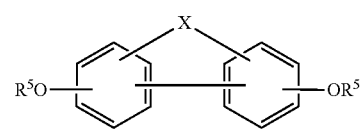
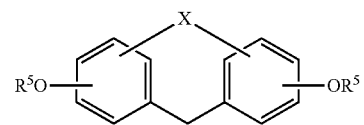
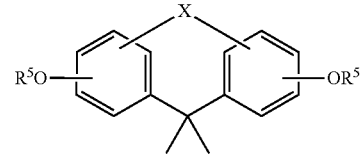
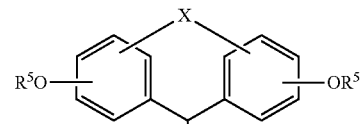
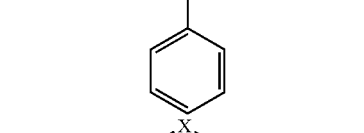
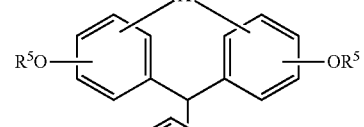
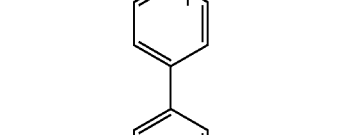
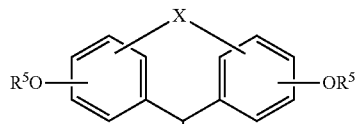
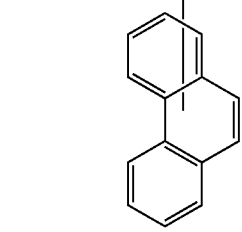
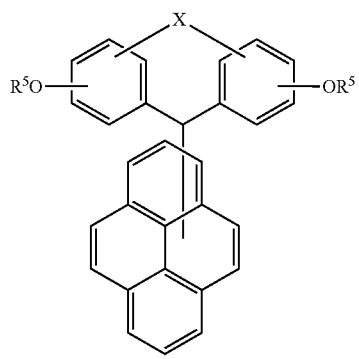
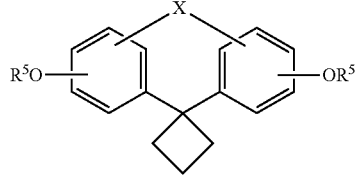
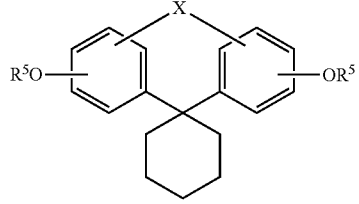
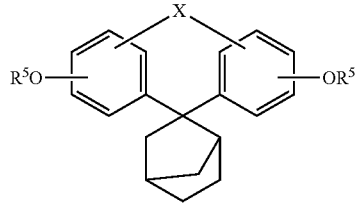
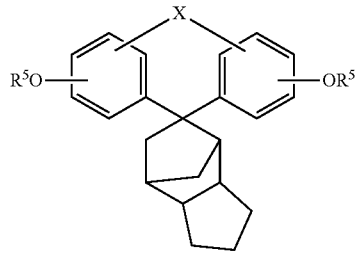

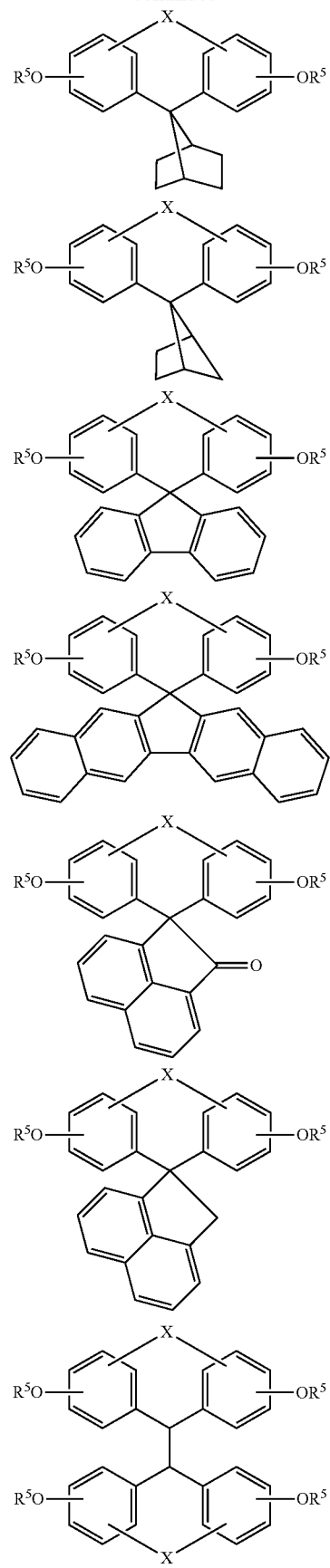
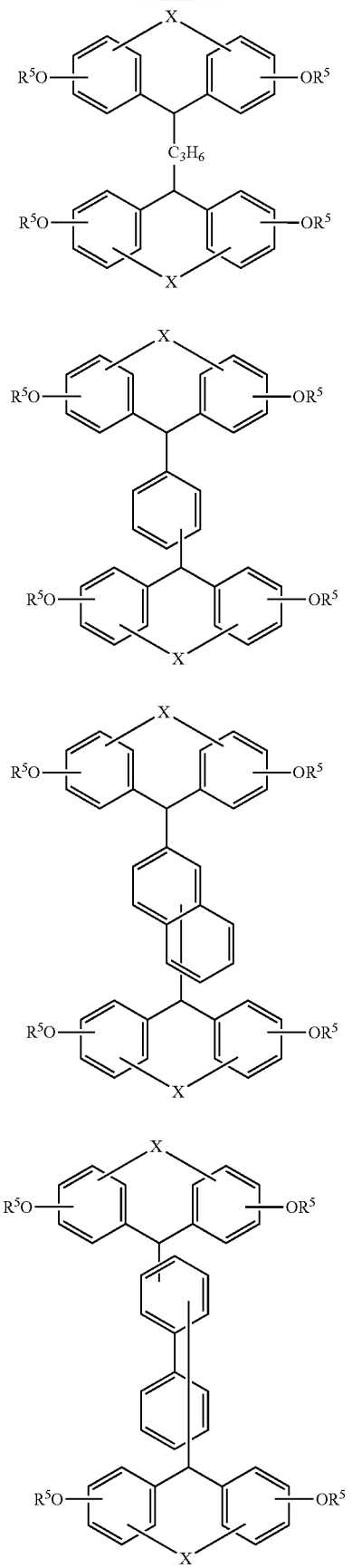

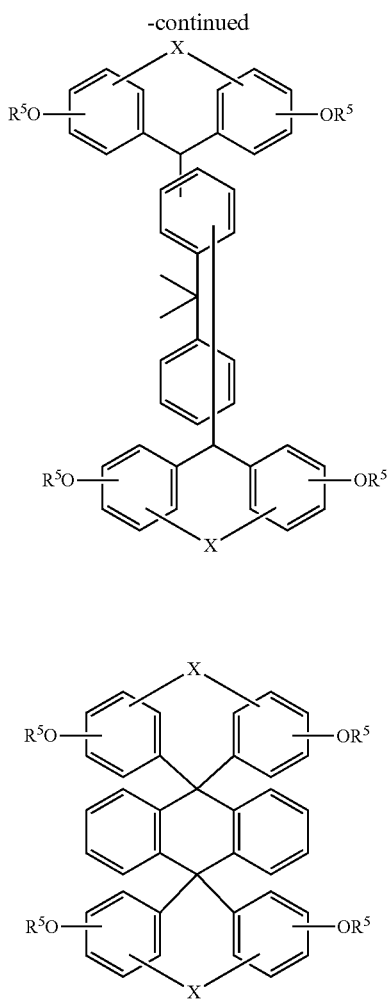

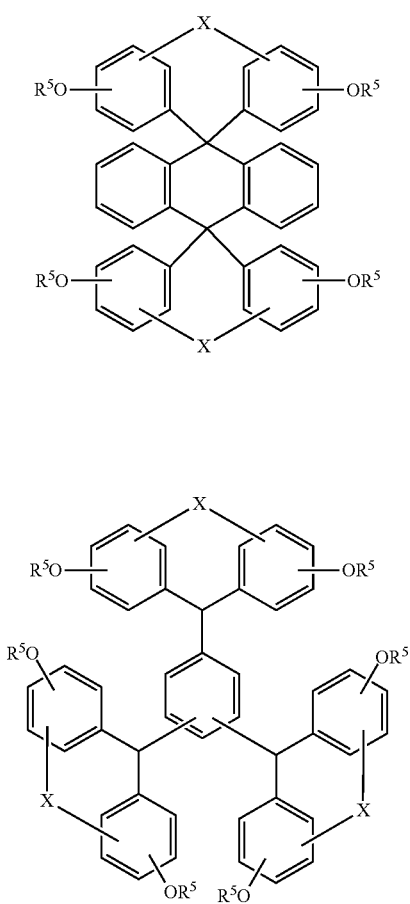

In the formula, X is the same as defined in the formula (1), and R⁵ is the same as defined in the formula (1A-1).

In addition, the compound represented by the formula (1A-2) is particularly preferably a compound represented by the following formula (BisN-1-CH1) or the following formula (BisN-1-CH2) from the viewpoint of solubility.

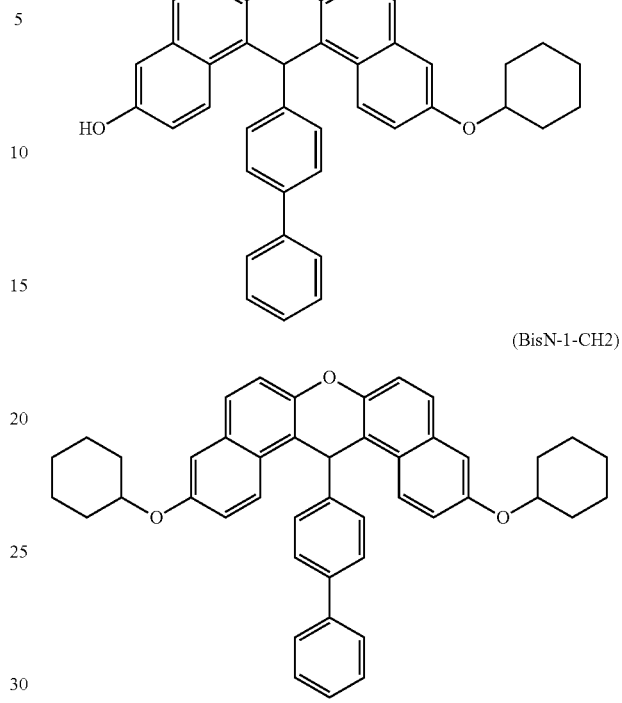

In addition, the compound represented by the formula (1A-2) is also preferably a compound represented by the following formula (BisN-1-PH1) or the following formula (BisN-1-PH2) from the viewpoint of solubility.

The compound represented by the formula (1) can be appropriately synthesized by applying a known method, and a synthesis method thereof is not particularly limited. For example, phenols or thiophenols corresponding to the structure of a desired compound, and aldehydes or ketones corresponding to the structure of a desired compound can be subjected to a polycondensation reaction under ordinary pressure in the presence of an acid catalyst to thereby provide the compound represented by the formula (1). The reaction can also be performed under pressure, if necessary. The reaction conditions can be modified to thereby control the production rates of a structure in which X represents crosslinking and a structure in which X represents non-crosslinking. For example, when the reaction temperature is higher, the reaction time is longer and the acid strength of the acid catalyst is higher, the production rate of the structure in which X represents crosslinking tends to be higher. On the other hand, when the reaction temperature is lower, the reaction time is shorter and the acid strength of the acid catalyst is lower, the production rate of the structure in which X represents non-crosslinking is higher. When a high solvent solubility is more important, the rate of the structure in which X represents non-crosslinking is preferably higher, and on the other hand, when a high heat resistance is more important, the rate of the structure in which X represents crosslinking is preferably higher.

Examples of the phenols include phenol, methylphenol, methoxybenzene, catechol, resorcinol and hydroquinone, but are not particularly limited thereto. These can be used singly or in combinations of two or more thereof. Among them, hydroquinone is more preferably used from the viewpoint that a xanthene structure can be easily made.

Examples of the thiophenols include benzenethiol, methylbenzenethiol, methoxybenzenethiol and benzenedithiol, but are not particularly limited thereto. These can be used singly or in combinations of two or more thereof. Among them, benzenedithiol is more preferably used from the viewpoint that a thioxanthene structure can be easily made.

Examples of the aldehydes include formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane and benzenetricarboxaldehyde, but are not particularly limited thereto. These can be used singly or in combinations of two or more thereof. Among them, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane or benzenetricarboxaldehyde is preferably used from the viewpoint of imparting a high heat resistance.

Examples of the ketones include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, but are not particularly limited thereto. These can be used alone, or two or more thereof can be used in combination. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of imparting a high heat resistance.

The acid catalyst for use in the above reaction can be appropriately selected from known ones and used, and is not particularly limited. Such an acid catalyst is an inorganic acid or an organic acid, as widely known, and specific examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones, as long as the reaction of the aldehydes or ketones to be used and the phenols or thiophenols to be used progresses. Examples thereof include water, methanol, ethanol, propanol, butanol, tetrahydrofuran, dioxane, ethylene glycol dimethyl ether, ethylene glycol diethyl ether, or a mixed solvent thereof. Herein, such a solvent can be used singly or in combinations of two or more thereof. In addition, the amount of such a solvent to be used can be appropriately set depending on the types of raw materials to be used and the acid catalyst to be used, reaction conditions, and the like. The amount of the solvent to be used is not particularly limited, but the amount is preferably in the range from 0 to 2000 parts by mass based on 100 parts by mass of reaction raw materials. Furthermore, the reaction temperature in the above reaction can be appropriately selected depending on the reactivity of reaction raw materials. The reaction temperature is not particularly limited, but is usually in the range from 10 to 200° C. In order to form a xanthene structure or a thioxanthene structure as the compound represented by the general formula (1) of the present embodiment, the reaction temperature is preferably high and, specifically, preferably ranges from 60 to 200° C. Herein, the reaction method that can be used is appropriately selected from known methods, and is not particularly limited, but includes a method in which the phenols or thiophenols, the aldehydes or ketones, and the acid catalyst are charged at once, and a method in which the phenols, thiophenols, aldehydes or ketones are dropped in the presence of the acid catalyst. After completion of the polycondensation reaction, the resulting compound can be isolated according to an ordinary method, and the isolation method is not particularly limited. For example, in order to remove the unreacted raw materials and the acid catalyst present in the system, a common method in which the temperature in a reaction tank is raised to 130 to 230° C. to remove a volatile content at about 1 to 50 mmHg can be adopted to thereby provide an objective compound.

The reaction progresses under a preferable reaction condition in which 1 mol to an excess amount of the phenols or thiophenols and 0.001 to 1 mol of the acid catalyst are used based on 1 mol of the aldehydes or ketones at ordinary pressure and at 50 to 150° C. for about 20 minutes to 100 hours.

After completion of the reaction, the objective compound can be isolated by a known method. For example, the objective compound, a compound serving as a precursor of the compound represented by the formula (1), can be obtained by concentrating a reaction liquid, adding pure water to thereby precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

The objective compound, the compound represented by the formula (1), can be obtained by, for example, subjecting the precursor compound obtained in the above method to substitution of a hydrogen atom of at least one phenolic hydroxyl group with a monovalent group having 1 to 30 carbon atoms by a known method.

The method for substituting a hydrogen atom of a phenolic hydroxyl group with a monovalent group having 1 to 30 carbon atoms is not particularly limited, and for example, a dehydrohalogenation reaction in which a halogenated hydrocarbon compound is reacted with the precursor compound in the presence of a basic catalyst can be performed.

The halogenated hydrocarbon compound is not particularly limited, and a halogenated hydrocarbon compound having 1 to 30 carbon atoms is suitably used. The halogenated hydrocarbon compound includes a straight hydrocarbon group, a branched hydrocarbon group, an alicyclic hydrocarbon group, an aromatic hydrocarbon group and a group including a combination of two or more thereof, as well as a halogen atom. Herein, the alicyclic hydrocarbon group also includes a bridged cyclic hydrocarbon group. The halogenated hydrocarbon compound may also have a double bond, a hetero atom, or other halogen atom.

Examples of the halogenated hydrocarbon compound include methyl chloride, methyl bromide, methyl iodide, propyl chloride, propyl bromide, propyl iodide, butyl chloride, butyl bromide, butyl iodide, heptyl chloride, heptyl bromide, heptyl iodide, hexyl chloride, hexyl bromide, hexyl iodide, decyl chloride, decyl bromide, decyl iodide, or a group including a compound represented by the following formula (5), but are not particularly limited thereto. These can be used singly or in combinations of two or more thereof.

(5)

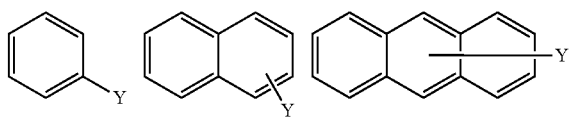

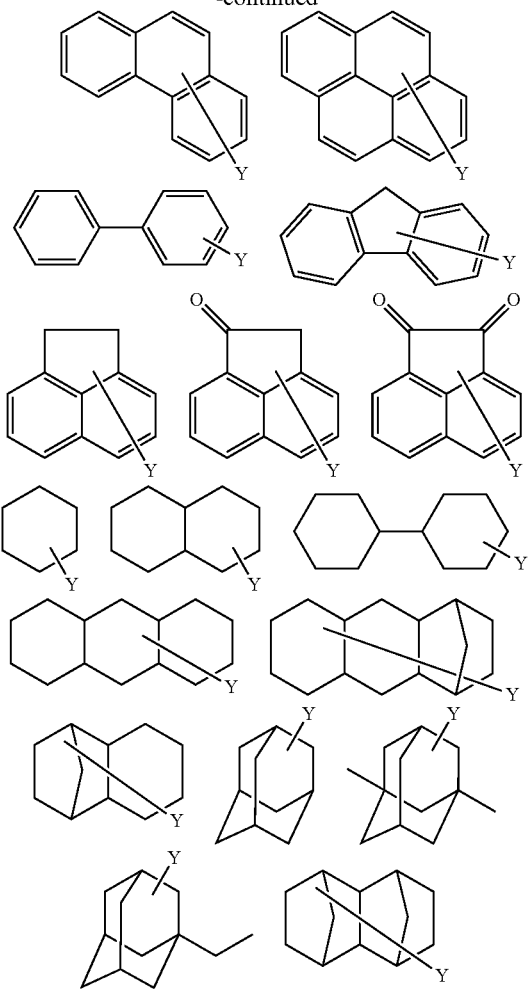

In the formula (5), Y represents a chlorine atom, a bromine atom, or an iodine atom.

A reaction of 0.1 to 10 mol of the halogenated hydrocarbon compound based on 1 mol of the precursor compound is performed in an organic solvent such as dimethylformamide in the presence of a basic catalyst (sodium carbonate, potassium carbonate, triethylamine, ammonia, sodium hydroxide, or the like) at 0 to 150° C. for about 0.5 to 20 hours. The reaction can allow at least one phenolic hydroxyl group in the resulting precursor compound to be converted to an alkoxyl group. Then, the resultant is subjected to separation by filtration, washing with alcohols such as methanol, washing with water, and filtration, and thereafter drying, to thereby provide the compound represented by the formula (1).

The molecular weight of the compound represented by the formula (1) is not particularly limited, and the weight average molecular weight Mw is preferably 350 to 5,000, more preferably, 400 to 3,000. Herein, the Mw can be measured by a method in Examples described later.

[Resin]

The compound represented by the formula (1) can be used as a material for forming an underlayer film for lithography, as it is. In addition, the compound can also be used as a resin obtained with the compound represented by the formula (1) as a monomer. For example, the compound can also be used as a resin obtained by reacting the compound represented by the formula (1) with a compound having crosslinking reactivity. Examples of the resin obtained with the compound represented by the formula (1) as a monomer include those having a structure represented by the following formula (2). That is, a material for forming an underlayer film for lithography of the present embodiment may also be one containing a resin having a structure represented by the following formula (2).

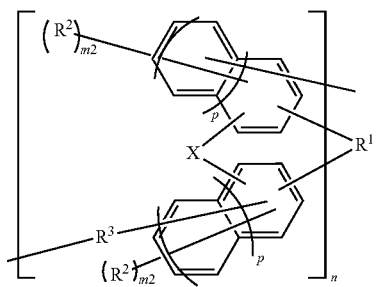

(2)

(in formula (2), each X independently represents an oxygen atom or a sulfur atom, or non-crosslinking, $R^1$ represents a single bond or a 2n-valent group having 1 to 30 carbon atoms, the hydrocarbon group may also have an alicyclic hydrocarbon group, a double bond, a hetero atom, or an aryl group having 6 to 30 carbon atoms, each $R^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one $R^2$ represents an alkoxy group having 1 to 30 carbon atoms or an aryloxy group having 6 to 30 carbon atoms, each $R^3$ independently represents a single bond, or a straight or branched alkylene group having 1 to 20 carbon atoms, each $m^2$ is independently an integer of 1 to 5, p is independently 0 or 1, and n is an integer of 1 to 4.)

In the formula (2), each X independently represents an oxygen atom or a sulfur atom, or non-crosslinking. Here, the case where X represents non-crosslinking means that the compound represented by the formula (2) has a structure represented by the following formula (2B).

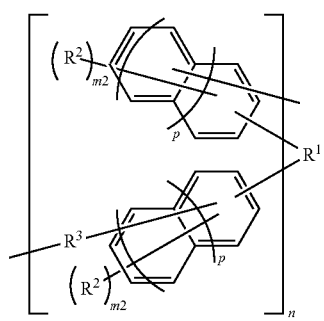

(2B)

(in formula (2B), $R^1$, $R^2$, $R^3$, $m^2$, n and p are the same as those described above.)

In the formula (2), $R^1$ represents a single bond or a 2n-valent group having 1 to 30 carbon atoms, and respective aromatic rings are bonded to each other via $R^1$. Herein, the 2n-valent group may have an alicyclic hydrocarbon group, a double bond, a hetero atom, or an aryl group having 6 to 30 carbon atoms.

Each $R^2$ independently represents a monovalent group selected from the group consisting of a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms and a hydroxyl group, and $m^2$ of $R^2$(s) are bonded to an aromatic ring. Herein, at least one $R^2$ represents an alkoxy group having 1 to 30 carbon atoms or an aryloxy group having 6 to 30 carbon atoms.

Each $R^3$ independently represents a single bond, or a straight or branched alkylene group having 1 to 20 carbon atoms.

Each $m^2$ is independently an integer of 1 to 5, each p is independently 0 or 1, and n is an integer of 1 to 4. Herein, the 2n-valent group means the same as described in the formula (1).

Herein, the structure represented by the formula (2) is preferably a structure represented by the following formula (2A) from the viewpoint of an enhancement in heat resistance derived from rigid structure formation.

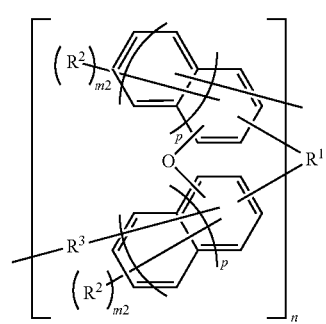

(2A)

(in formula (2A), $R^1$, $R^2$, $R^3$, $m^2$, n and p are the same as those described above.)

Herein, the structure represented by the formula (2A) is preferably a structure represented by the following formula (2A-1) from the viewpoint of an enhancement in heat resistance by an enhancement in the degree of crosslinking during baking, derived from $R^5O$ group introduction.

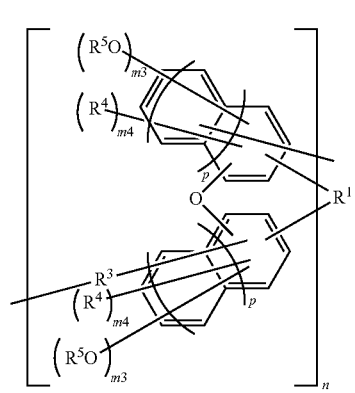

(2A-1)

(in formula (2A-1), $R^1$, $R^4$, $R^5$, $m^3$, $m^4$, n and p are the same as those described above.)

In addition, the structure represented by the formula (2B) is preferably a structure represented by the following formula (2B-1) from the viewpoint of an enhancement in solubility in a safe solvent.

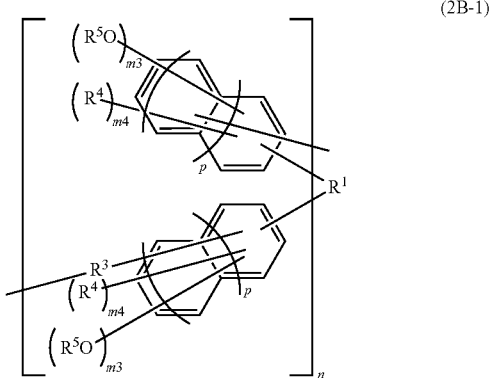

(2B-1)

(in formula (2B-1), $R^1$, $R^4$, $R^5$, $m^3$, $m^4$, n and p are the same as those described above.)

The compound having crosslinking reactivity is not particularly limited as long as it can provide an oligomer of the compound represented by the formula (1), and known one can be used therefor. Specific examples thereof include aldehyde, ketone, carboxylic acid, carboxylic halide, a halogen-containing compound, an amino compound, an imino compound, isocyanate, and an unsaturated hydrocarbon group-containing compound, but are not particularly limited thereto.

Specific examples of the resin having the structure represented by the formula (2) include, but are not limited to the following, a novolac resin obtained by a condensation reaction and the like of the compound represented by the formula (1) with an aldehyde as the compound having crosslinking reactivity.

Herein, examples of the aldehyde for use in forming the novolac resin of the compound represented by the formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not particularly limited thereto. Among them, formaldehyde is preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol, based on 1 mol of the compound represented by the formula (1).

An acid catalyst can also be used in the condensation reaction of the compound represented by the formula (1) with an aldehyde. The acid catalyst that can be here used is appropriately selected from known ones, and is not particularly limited. Such an acid catalyst is an inorganic acid or an organic acid, as widely known, and specific examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the acid catalyst to be used, reaction conditions, and the like, and is not particularly limited, but the amount is preferably 0.01 to 100 parts by mass based on 100 parts by mass of reaction raw materials. Herein, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, no aldehydes may be used.

A reaction solvent can also be used in the condensation reaction of the compound represented by the formula (1) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, or a mixed solvent thereof. Herein, these solvents can be used alone, or two or more thereof can be used in combination.

In addition, the amount of the solvent to be used can be appropriately set depending on the types of raw materials to be used and the acid catalyst to be used, reaction conditions, and the like. The amount of the solvent to be used is not particularly limited, but is preferably in the range from 0 to 2000 parts by mass based on 100 parts by mass of reaction raw materials.

Furthermore, the reaction temperature can be appropriately selected depending on the reactivity of reaction raw materials, and is not particularly limited. The reaction temperature usually ranges from 10 to 200° C. Herein, the reaction method that can be used is appropriately selected from known methods, and is not particularly limited, but includes a method in which the compound represented by the formula (1), the aldehydes, and the catalyst are charged at once, and a method in which the compound represented by the formula (1) and the aldehydes are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective novolac resin.

Herein, the resin having the structure represented by the formula (2) may be a homopolymer of the compound represented by the formula (1), or may be a copolymer with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not particularly limited thereto.

In addition, the resin having the structure represented by the formula (2) may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not particularly limited thereto. Herein, the resin having the structure represented by the formula (2) may be a bi or higher functional (for example, bi to tetra) copolymer of the compound represented by the formula (1) with the above-described phenols, may be a bi or higher functional (for example, bi to tetra) copolymer of the compound represented by the formula (1) with the above-described copolymerizable monomer, or may be a ter or higher (for example, ter to tetra) copolymer of the compound represented by the formula (1) with the above-described phenols and the above-described copolymerizable monomer.

Herein, the molecular weight of the resin having the structure represented by the formula (2) is not particularly limited, and the weight average molecular weight (Mw) in terms of polystyrene is preferably 500 to 30,000, and more preferably 750 to 20,000. In addition, the resin having the structure represented by the formula (2) preferably has a dispersity (weight average molecular weight Mw/number average molecular weight Mn) in a range from 1.2 to 7, with respect to the molecular weight thereof, from the viewpoints of improving a crosslinking efficiency and suppressing a volatile component during baking.

The compound represented by the formula (1) and/or the resin having the structure represented by the formula (2) preferably have/has a high solubility in the solvent from the viewpoint of making the application of a wet process easier. More specifically, the compound and/or the resin preferably have/has a solubility of 10% by mass or more in 1-methoxy-2-propanol (PGME) or propylene glycol monomethyl ether acetate (PGMEA). Herein, the solubility in PGME or PGMEA is defined as "Mass of compound and/or resin/ (Mass of compound and/or resin+Mass of solvent)×100(% by mass)". For example, in the case where 10 g of the compound and/or the resin are/is evaluated to be dissolved in 90 g of PGMEA, the solubility of the compound and/or the resin in PGMEA is "10% by mass or more", and in the case where the compound and/or the resin are/is evaluated not to be dissolved, the solubility is "less than 10% by mass".

[Material for Forming Underlayer Film for Lithography]

A material for forming an underlayer film for lithography of the present embodiment contains at least one substance selected from the group consisting of the compound of the present embodiment and the resin of the present embodiment. More specifically, the material for forming an underlayer film for lithography of the present embodiment contains at least one substance selected from the group consisting of the compound represented by the formula (1) and a resin obtained by a reaction of the compound represented by the formula (1) with the compound having crosslinking reactivity.

When the material for forming an underlayer film for lithography of the present embodiment includes an organic solvent as an optional component described later, the content of the compound of the present embodiment and/or the resin of the present embodiment is not particularly limited, but is preferably 1 to 33 parts by mass, more preferably 2 to 25 parts by mass, further preferably 3 to 20 parts by mass, based on 100 parts by mass of the total amount of the components including the organic solvent.

The material for forming an underlayer film for lithography of the present embodiment may include, if necessary, other component such as a crosslinking agent, an acid generating agent, and an organic solvent. Hereinafter, these optional components will be described.

[Crosslinking Agent]

The material for forming an underlayer film for lithography of the present embodiment may contain, if necessary, a crosslinking agent from the viewpoint of suppression of intermixing, and the like. Specific examples of the crosslinking agent usable in the present embodiment include a melamine compound, a guanamine compound, a glycoluril compound or a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, but are not particularly limited thereto. Herein, these crosslinking agents can be used singly or in combinations of two or more thereof. In addition, such a crosslinking agent may also be used as an additive, or may also be introduced as a pendant group into a polymer side chain. A compound including a hydroxy group can also be used as the crosslinking agent.

Specific examples of the melamine compound include, but are not limited to the following, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, but are not limited to the following, tris(2,3-epoxypropyl)isocyanurate, trimethylolmethane triglycidyl ether, trimethylolpropane triglycidyl ether, and triethylolethane triglycidyl ether.

Specific examples of the guanamine compound include, but are not limited to the following, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, but are not limited to the following, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, but are not limited to the following, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, but are not limited to the following, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

The content of the crosslinking agent in the material for forming an underlayer film for lithography of the present embodiment is not particularly limited, but is preferably 5 to 50 parts by mass, more preferably 10 to 40 parts by mass, based on 100 parts by mass of the content of the compound of the present embodiment and/or the resin of the present embodiment. The content is set within the above preferable range to result in tendencies to suppress the occurrence of the mixing phenomenon with the resist layer, and to result in tendencies to enhance an antireflective effect and improve film formability after crosslinking.

[Acid Generating Agent]

The material for forming an underlayer film for lithography of the present embodiment may also contain, if necessary, an acid generating agent from the viewpoint of further promoting a crosslinking reaction by heat. As the acid generating agent in the art, one for generating an acid by pyrolysis and one for generating an acid by light irradiation are known, and any of them can be used.

The acid generating agent includes:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not particularly limited thereto. Herein, these acid generating agents can be used alone, or two or more thereof can be used in combination.

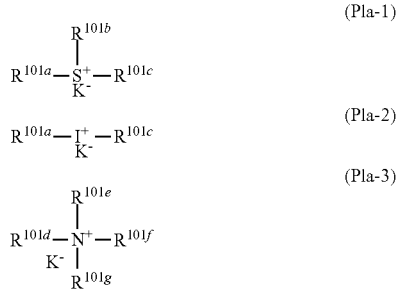

In the above formulae, each of $R^{101a}$, $R^{101b}$ and $R^{101c}$ independently represents a straight, branched or cyclic alkyl group, alkenyl group, oxoalkyl group or oxoalkenyl group having 1 to 12 carbon atoms, an aryl group having 6 to 20 carbon atoms, or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group, alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group, alkylnaphthyl groups such as a methylnaphthyl group and an ethylnaphthyl group, alkoxynaphthyl groups such as a methoxynaphthyl group and an ethoxynaphthyl group, dialkylnaphthyl groups such as a dimethylnaphthyl group and a diethylnaphthyl group, and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion, fluoroalkyl sulfonates such as triflate, 1,1,1-trifluoroethane sulfonate, and nonafluorobutane sulfonate, aryl sulfonates such as tosylate, benzene sulfonate, 4-fluorobenzene sulfonate, and 1,2,3,4,5-pentafluorobenzene sulfonate, and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include, but are not limited to the following, imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, triethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generating agent and a thermal acid generating agent. The onium salt of the formula (P1a-3) has a function as a thermal acid generating agent.

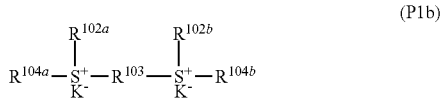

(P1b)

In the formula (P1b), each of $R^{102a}$ and $R^{102b}$ independently represents a straight, branched or cyclic alkyl group having 1 to 8 carbon atoms. $R^{103}$ represents a straight, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

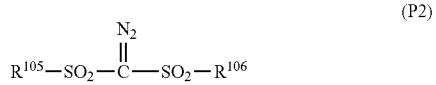

(P2)

In the formula (P2), each of $R^{105}$ and $R^{106}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group, and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

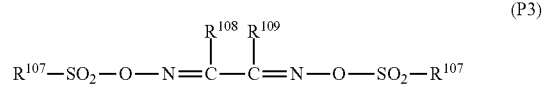

(P3)

In the formula (P3), each of $R^{107}$, $R^{108}$ and $R^{109}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a straight or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

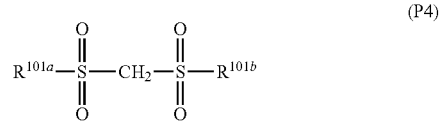

(P4)

(In the formula (P4), $R^{101a}$ and $R^{101b}$ are the same as those described above.)

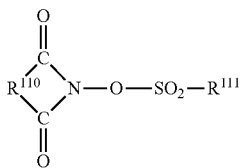

(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a straight or branched alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group, or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generating agent include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl) diphenylsulfonium trifluoromethanesulfonate, bis(p-tert-butoxyphenyl)phenylsulfonium trifluoromethanesulfonate, tris (p-tert-butoxyphenyl)sulfonium trifluoromethanesulfonate, triphenylsulfonium p-toluenesulfonate, (p-tert-butoxyphenyl) diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl) sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis [methyl(2-oxocyclopentyl)sulfonium trifluoromethanesulfonate], and 1,2'-naphthylcarbonylmethyltetrahydrothiophenium triflate, diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl) diazomethane, bis(sec-butylsulfonyl)diazomethane, bis(n-propylsulfonyl)diazomethane, bis(isopropylsulfonyl) diazomethane, bis(tert-butylsulfonyl)diazomethane, bis(n-amylsulfonyl)diazomethane, bis(isoamylsulfonyl) diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane, glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α- dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime, bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane, β-ketosulfone derivatives such as 2-cyclohexylcarbonyl-2-(p-toluenesulfonyl)propane and 2-isopropylcarbonyl-2-(p-toluenesulfonyl)propane, disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate, sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene, and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate, diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane, glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane, and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester are preferably used.

The content of the acid generating agent in the material for forming an underlayer film for lithography of the present embodiment is not particularly limited, but is preferably 0.1 to 50 parts by mass, more preferably 0.5 to 40 parts by mass, based on 100 parts by mass of the content of the compound of the present embodiment and/or the resin of the present embodiment. The content is set within the above range to result in a tendency to increase the acid generation amount to promote a crosslinking reaction, and also to result in a tendency to suppress the occurrence of the mixing phenomenon with a resist layer.

Furthermore, the material for forming an underlayer film for lithography of the present embodiment may contain a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not particularly limited thereto.

Specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

The content of the basic compound in the material for forming an underlayer film for lithography of the present embodiment is not particularly limited, but is preferably 0.001 to 2 parts by mass, more preferably 0.01 to 1 parts by mass, based on 100 parts by mass of the compound of the present embodiment and/or the resin of the present embodiment. The content is set within the above preferable range to result in a tendency to improve preservation stability without excessively interrupting a crosslinking reaction.

[Organic Solvent]

The material for forming an underlayer film for lithography of the present embodiment may also contain an organic solvent. A known organic solvent can be appropriately used as the organic solvent as long as it can dissolve at least the compound of the present embodiment and/or the resin of the present embodiment.

Specific examples of the organic solvent include ketone-based solvents such as acetone, methyl ethyl ketone, methyl isobutyl ketone and cyclohexanone, cellosolve-based solvents such as propylene glycol monomethyl ether and propylene glycol monomethyl ether acetate, ester-based solvents such as ethyl lactate, methyl acetate, ethyl acetate, butyl acetate, isoamyl acetate, methyl methoxypropionate and methyl hydroxyisobutyrate, alcohol-based solvents such as methanol, ethanol, isopropanol and 1-ethoxy-2-propanol, and aromatic hydrocarbons such as toluene, xylene and anisole, but are not particularly limited thereto. These organic solvents can be used singly or in combinations of two or more thereof.

Among the organic solvents, particularly preferable are cyclohexanone, propylene glycol monomethyl ether, propylene glycol monomethyl ether acetate, ethyl lactate, methyl hydroxyisobutyrate, and anisole, in terms of safety.

The content of the organic solvent is not particularly limited, but is preferably 100 to 10,000 parts by mass, more preferably 200 to 5,000 parts by mass, based on 100 parts by mass of the compound of the present embodiment and/or the resin of the present embodiment from the viewpoints of solubility and film formation.

[Other Component(s)]

In addition, the material for forming an underlayer film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the material for forming an underlayer film for lithography of the present embodiment can also contain a known additive such as an ultraviolet absorber, a surfactant, a colorant and a non-ionic surfactant.

[Underlayer Film for Lithography, and Multilayer Resist Pattern Forming Method]

An underlayer film for lithography of the present embodiment is formed from the material for forming an underlayer film for lithography of the present embodiment.

In addition, a resist pattern forming method of the present embodiment comprises step (A-1) of forming an underlayer film on a substrate by using the material for forming an underlayer film for lithography of the present embodiment, step (A-2) of forming at least one photoresist layer on the underlayer film, and step (A-3) of, after step (A-2), irradiating a predetermined region of the photoresist layer with radiation, followed by developing.

Furthermore, a circuit pattern forming method of the present embodiment comprises step (B-1) of forming an underlayer film on a substrate by using the material for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

The underlayer film for lithography of the present embodiment is not particularly limited in terms of the forming method thereof as long as it is formed from the material for forming an underlayer film for lithography described above, and a known method can be applied. For example, the underlayer film can be formed by applying the material for forming an underlayer film for lithography described above on the substrate by a known coating method or printing method such as spin coating or screen printing, and removing an organic solvent by volatilization or the like. The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm, more preferably 50 to 15,000 nm. After the underlayer film is prepared, in the case of a two-layer process, a silicon-containing resist layer or a usual single-layer resist including a hydrocarbon is preferably prepared on the underlayer film, and in the case of a three-layer process, a silicon-containing intermediate layer is preferably prepared on the underlayer film, and a single-layer resist layer not containing silicon is preferably prepared on the silicon-containing intermediate layer. In these cases, a photoresist material for forming the resist layer, which can be used, is a known one.

After the underlayer film is prepared on the substrate, in the case of a two-layer process, a silicon-containing resist layer or a usual single-layer resist including a hydrocarbon can be prepared on the underlayer film, and in the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material is preferably used, which contains a silicon atom-containing polymer such as a polysilsesquioxane derivative or a vinylsilane derivative used as a base polymer in the viewpoint of oxygen gas-etching resistance, and an organic solvent, an acid generating agent and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to allow reflection to be effectively suppressed. For example, if a material including many aromatic groups and having a high substrate-etching resistance is used for the underlayer film in a 193 nm exposure process, a k-value tends to be increased to increase substrate reflection rate, but the reflection can be suppressed by the intermediate layer to thereby make the substrate reflection rate 0.5% or less. For the intermediate layer having such an antireflection effect, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are used for protecting a side wall for preventing a pattern side wall from being undercut. On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. Examples of the nitride film forming method include, but not limited to the following, any method described in Japanese Patent Laid-Open No. 2002-334869 (Patent Literature 6) and WO2004/066377 (Patent Literature 7).

While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to allow reflection to be effectively suppressed. Examples of a specific material for the polysilsesquioxane-based intermediate layer include, but not limited to the following, any material described in Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate.

Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

[Purification Method of Compound or Resin]

A purification method of the compound or the resin of the present embodiment comprises a step of bringing a solution (A) comprising an organic solvent optionally immiscible with water, and the compound of the present embodiment or the resin of the present embodiment into contact with an acidic aqueous solution for extraction. The purification method of the present embodiment is configured as described above, and therefore can reduce the content of various metals that can be included as impurities in the compound of the present embodiment or the resin of the present embodiment.

More specifically, in the present embodiment, an extraction treatment can be performed by dissolving the compound or the resin in the organic solvent optionally immiscible with water, and further bringing the solution into contact with an acidic aqueous solution. Thus, a metal content included in the solution (A) can be transferred to an aqueous phase, and an organic phase and the aqueous phase can be then separated to thereby provide the compound of the present embodiment or the resin of the present embodiment, in which the metal content is reduced.

The compound of the present embodiment or the resin of the present embodiment may be subjected to the purification singly, but can also be subjected to the purification as a mixture of two or more. In addition, the compound of the present embodiment or the resin of the present embodiment may also contain various surfactants, various crosslinking agents, various acid generating agents, various stabilizers, and the like.

The organic solvent optionally immiscible with water, to be used in the present embodiment, is not particularly limited, but is preferably an organic solvent whose solubility in water at room temperature is less than 30%, more preferably less than 20%, particularly preferably less than 10%, and which can be safely applied to a semiconductor manufacturing process. The amount of the organic solvent to be used is usually about 1 to 100 times by mass the amount of the compound represented by the formula (1) to be used, or a resin obtained by a reaction of the compound represented by the formula (1) with the compound having crosslinking reactivity.

Specific examples of the solvent to be used include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PGMEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate and the like are preferable, methyl isobutyl ketone, ethyl acetate, cyclohexanone and propylene glycol monomethyl ether acetate are more preferable, and methyl isobutyl ketone and ethyl acetate are still more preferable. Methyl isobutyl ketone, ethyl acetate, and the like are relatively high in saturation solubility of compound of the present embodiment or the resin of the present embodiment and relatively low in the boiling point, and therefore can allow the burden in industrial distilling off of the solvent or in a step of removing the solvent by drying to be reduced.

These solvents can be used singly or as a mixture of two or more thereof.

The acidic aqueous solution to be used in the present embodiment is appropriately selected from aqueous solutions in which an organic or inorganic compound commonly known is dissolved in water. Examples include, but not limited to the following, an aqueous solution in which a mineral acid such as hydrochloric acid, sulfuric acid, nitric acid or phosphoric acid is dissolved in water, or an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of at least one mineral acid selected from the group consisting of hydrochloric acid, sulfuric acid, nitric acid and phosphoric acid, or an aqueous solution of at least one organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid is preferable, an aqueous solution of sulfuric acid, nitric acid and a carboxylic acid such as acetic acid, oxalic acid, tartaric acid and citric acid is more preferable, an aqueous solution of sulfuric acid, oxalic acid, tartaric acid or citric acid is further preferable, and an aqueous solution of oxalic acid is still more preferable. It is considered that a polyvalent carboxylic acid such as oxalic acid, tartaric acid and citric acid is coordinated with a metal ion to exert a chelating effect, and therefore tends to allow a metal to be more effectively removed. In addition, the water to be here used is preferably water having a low metal content according to the purpose of the present embodiment, such as ion-exchange water.

The pH of the acidic aqueous solution to be used in the present embodiment is not particularly limited, but the acidity of the aqueous solution is preferably adjusted in consideration of the effect on the compound of the present embodiment or the resin of the present embodiment. The pH is usually in the range from about 0 to 5, preferably about 0 to 3.

The amount of the acidic aqueous solution to be used in the present embodiment is not particularly limited, but the amount to be used is preferably adjusted from the viewpoint of reducing the number of extractions for metal removal and the viewpoint of ensuring operation property in consideration of the total amount of the liquid. The amount of the aqueous solution to be used is usually 10 to 200% by mass, preferably 20 to 100% by mass relative to the solution of the compound of the present embodiment or the resin of the present embodiment dissolved in the organic solvent, from the above viewpoints.

In the present embodiment, the acidic aqueous solution described above can be brought into contact with the solution including the compound of the present embodiment or the resin of the present embodiment and the organic solvent optionally immiscible with water, to thereby extract the metal content.

In the present embodiment, the solution (A) preferably further includes an organic solvent optionally miscible with water. When the organic solvent optionally miscible with water is included, the amount of the compound of the present embodiment or the resin of the present embodiment to be charged can be increased, and liquid separating property can be enhanced to result in a tendency to perform purification at a high pot efficiency. The method for adding the organic solvent optionally miscible with water is not particularly limited. For example, any of a method in which the organic solvent optionally miscible with water is added to the solution including the organic solvent in advance, a method in which the organic solvent optionally miscible with water is added to water or the acidic aqueous solution in advance, and a method in which the organic solvent optionally miscible with water is added after the solution including the organic solvent is brought into contact with water or the acidic aqueous solution may be adopted. Among them, a method in which the organic solvent optionally miscible with water is added to the solution including the organic solvent in advance is preferable in terms of operation workability and ease of maintenance of the amount to be charged.

The organic solvent optionally miscible with water, to be used in the present embodiment, is not particularly limited, but is preferably an organic solvent that can be safely applied to a semiconductor manufacturing process. The amount of the organic solvent optionally miscible with water, to be used, is not particularly limited as long as a solution phase and an aqueous phase are separated, but is usually 0.1 to 100 times by mass the amount of the compound of the present embodiment or the resin of the present embodiment.

Specific examples of the solvent optionally miscible with water, to be used in the present embodiment, include, but are not limited to the following, ethers such as tetrahydrofuran and 1,3-dioxolane, alcohols such as methanol, ethanol and isopropanol, ketones such as acetone and N-methylpyrrolidone, glycol ethers such as ethylene glycol monoethyl ether, ethylene glycol monobutyl ether, propylene glycol monomethyl ether (PGME) and propylene glycol monoethyl ether, and aliphatic hydrocarbons. Among them, N-methylpyrrolidone, propylene glycol monomethyl ether, and the like are preferable, and N-methylpyrrolidone and propylene glycol monomethyl ether are more preferable. These solvents can be used singly or as a mixture of two or more thereof.

In the present embodiment, the temperature in bringing of the solution (A) into contact with the acidic aqueous solution, namely, in performing of an extraction treatment is usually in the range from 20 to 90° C., preferably 30 to 80° C. The extraction operation is not particularly limited, but is performed by, for example, well mixing with stirring or the like and thereafter standing. Thus, the metal content included in the solution including the compound of the present embodiment or the resin of the present embodiment and the organic solvent is transferred to the aqueous phase. In addition, the operation can allow the acidity of the solution to be reduced, suppressing the deterioration of properties of the compound of the present embodiment or the resin of the present embodiment.

The mixed solution is separated to the solution phase including the compound of the present embodiment or the resin of the present embodiment and the organic solvent, and the aqueous phase by standing, and therefore the solution including the compound of the present embodiment or the resin of the present embodiment and the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

In the present embodiment, after the extraction treatment by the step of bringing the solution (A) into contact with the acidic aqueous solution is performed, a step of further performing an extraction treatment with water is preferably performed. That is, after the extraction treatment with the acidic aqueous solution is performed, the solution including the compound of the present embodiment or the resin of the present embodiment and the organic solvent, extracted and recovered from the aqueous solution, is preferably further subjected to an extraction treatment with water. The extraction treatment with water is not particularly limited, but can be performed by, for example, well mixing with stirring or the like and thereafter standing. The solution obtained after the standing is separated to the solution phase including the compound of the present embodiment or the resin of the present embodiment and the organic solvent, and the aqueous phase, and therefore the solution phase including the compound of the present embodiment or the resin of the present embodiment and the organic solvent can be recovered by decantation or the like.

In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including the compound of the present embodiment or the resin of the present embodiment and the organic solvent, can be easily removed by performing an operation such as distillation under reduced pressure. In addition, an organic solvent can be if necessary added to adjust the concentration of the compound of the present embodiment or the resin of the present embodiment to any concentration.

The method of isolating the compound of the present embodiment or the resin of the present embodiment from the resulting solution including the compound of the present embodiment or the resin of the present embodiment and the organic solvent is not particularly limited, and can be performed by a known method such as removal under reduced pressure, separation by reprecipitation and a combination thereof. If necessary, a known treatment such as a concentration operation, a filtration operation, a centrifugation operation and a drying operation can be performed.

EXAMPLES

Hereinafter, the present embodiment will be described by Synthesis Examples and Examples in more detail, but the present embodiment is not limited thereto at all.

(Carbon Concentration and Oxygen Concentration)

The carbon concentration and the oxygen concentration (% by mass) were measured by organic element analysis.

Apparatus: CHN CORDER MT-6 (manufactured by Yanaco Bunseki Kogyo Co.)

(Molecular Weight)

Measurement was performed by GC-MS analysis using Agilent 5975/6890N manufactured by Agilent Technologies. Alternatively, measurement was performed by LC-MS analysis using Acquity UPLC/MALDI-Synapt HDMS manufactured by Water.

(Molecular Weight Measurement)

The molecular weight was determined by field desorption mass spectrometry (FD-MS) analysis.

(Molecular Weight in terms of Polystyrene)

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 mL/min

Temperature: 40° C.

(Pyrolysis Temperature (Tg))

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg), and the heat resistance was evaluated according to the following criteria.

Evaluation A: pyrolysis temperature≥150° C.

Evaluation C: pyrolysis temperature<150° C.

(Solubility)

Each compound was dissolved at 23° C. so as to be provided as a 5% by mass solution in cyclohexanone (CHN), thereafter the solution was left to stand at 5° C. for 30 days, and the results were evaluated according to the following criteria.

Evaluation A: no precipitate was visually confirmed

Evaluation C: any precipitate was visually confirmed

Synthesis Example 1 Synthesis of BisN-1

To a container having an inner volume of 1000 mL, equipped with a stirrer, a condenser and a burette, were charged 16.0 g (100 mmol) of 2,6-naphthalenediol (reagent produced by Sigma-Aldrich Co., LLC.), 18.2 g (100 mmol) of 4-biphenylaldehyde (produced by Mitsubishi Gas Chemical Company, Inc.) and 300 mL of methyl isobutyl ketone, 50 mL of 95% sulfuric acid was added thereto, and the reaction liquid was stirred at 100° C. for 6 hours to perform a reaction. Then, the reaction liquid was concentrated, 500 g of pure water was added to precipitate a reaction product, and the resultant was cooled to room temperature followed by filtration for separation. A solid obtained by filtration was dried, and thereafter separated and purified by column chromatography to thereby provide 30.5 g of an objective compound (BisN-1) represented by the following formula.

Herein, the following peaks were observed by 400 MHz-1H-NMR, and it was confirmed that the compound had a chemical structure of the following formula. In addition, 2,6-dihydroxynaphthol was confirmed to be substituted at the 1-position based on doublet signals of protons at the 3-position and the 4-position.

1H-NMR: (d-DMSO, internal standard TMS)
δ (ppm) 9.7 (2H, O—H), 7.2 to 8.5 (19H, Ph-H), 6.6 (1H, C—H)

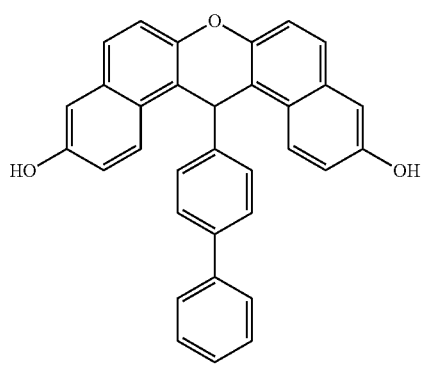

(BisN-1)

Synthesis Experimental Example 1 Synthesis of BisN-1-CH1 and BisN-1-CH2

To a container having an inner volume of 1000 mL, equipped with a stirrer, a condenser and a burette, were charged 11.7 g (25 mmol) of BisN-1 obtained above, 108 g (810 mmol) of potassium carbonate and 200 mL of dimethylformamide, 250 g (1.53 mol) of bromocyclohexane was added thereto, and the reaction liquid was stirred at 110° C. for 24 hours to perform a reaction. Then, the reaction liquid was concentrated, 500 g of pure water was added to precipitate a reaction product, and the resultant was cooled to room temperature followed by filtration for separation. The resulting solid was filtered and dried, and thereafter separated and purified by column chromatography to thereby provide 2.4 g and 9.6 g of objective compounds (BisN-1-CH1) and (BisN-1-CH2) represented by the following formulae, respectively.

The resulting compounds were subjected to NMR measurement in the measurement conditions, and thus the following peaks were observed and it was confirmed that the compounds had respective chemical structures of the following formulae.

BisN-1-CH1: δ (ppm) 9.7 (1H, O—H), 7.2 to 8.5 (19H, Ph-H), 6.6 (1H, C—H), 1.4 to 4.5 (11H, Cy-H)

Herein, Cy-H means a signal of proton of a cyclohexyl group.

BisN-1-CH2: δ (ppm) 7.2 to 8.5 (19H, Ph-H), 6.6 (1H, C—H), 1.4 to 4.5 (22H, Cy-H)

Herein, Cy-H means a signal of proton of a cyclohexyl group.

The molecular weight of BisN-1-CH1 obtained was 548. In addition, the carbon concentration and the oxygen concentration thereof were 85.3% by mass and 8.8% by mass, respectively.

The molecular weight of BisN-1-CH2 obtained was 630. In addition, the carbon concentration and the oxygen concentration thereof were 85.7% by mass and 7.6% by mass, respectively.

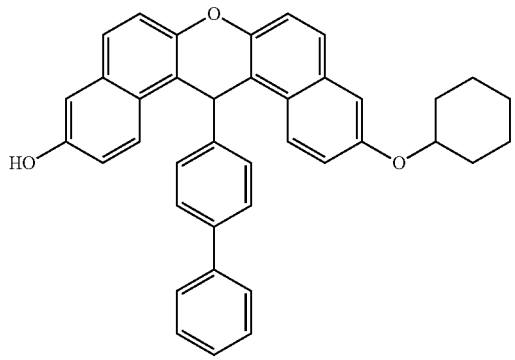

(BisN-1-CH1)

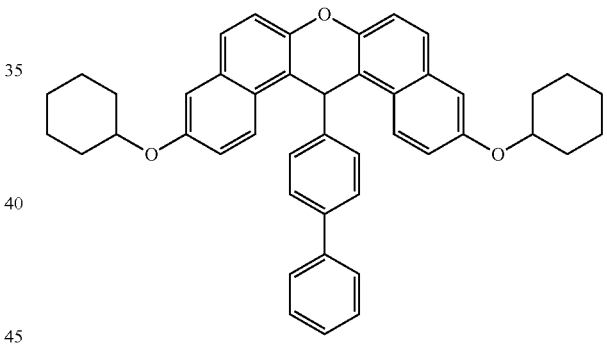

(BisN-1-CH2)

Synthesis Experimental Example 2 Synthesis of BisN-1-PH1

To a container having an inner volume of 1000 mL, equipped with a stirrer, a condenser and a burette, were charged 9.3 g (20 mmol) of BisN-1 obtained above, 26 g (80 mmol) of cesium carbonate, 0.8 g (4 mmol) of copper iodide, 1.7 g (12 mmol) of dimethyl glycine hydrochloride and 80 mL of dioxane, 8.2 g (40 mmol) of iodobenzene was added thereto, and the reaction liquid was stirred at 90° C. for 6 hours to perform a reaction. Then, 500 mL of ethyl acetate was added to precipitate a reaction product, and the resultant was cooled to room temperature followed by filtration for separation. The resulting solid was filtered and dried, and thereafter separated and purified by column chromatography to thereby provide 7.2 g of an objective compound (BisN-1-PH1) represented by the following formula.

The resulting compound was subjected to NMR measurement in the measurement conditions, and thus the following peaks were observed and it was confirmed that the compound had a chemical structure of the following formula.

BisN-1-PH1: δ (ppm) 9.2 (1H, O—H), 6.7 to 7.8 (24H, Ph-H), 5.3 (1H, C—H)

(BisN-1-PH1)

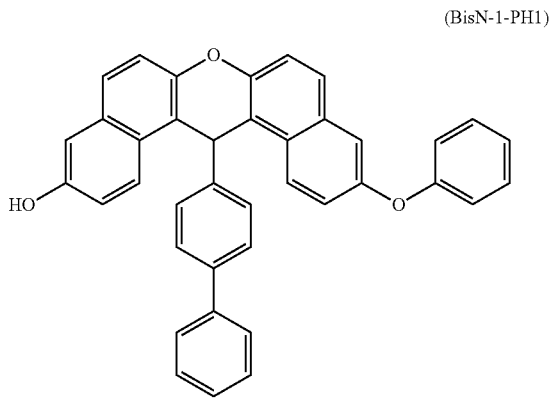 [SMILES: Oc1ccc2c3c(ccc2c1)Oc1ccc2cc(Oc4ccccc4)ccc2c1C3c1ccc(-c2ccccc2)cc1]

Synthesis Experimental Example 3 Synthesis of BisN-1-PH2

To a container having an inner volume of 1000 mL, equipped with a stirrer, a condenser and a burette, were charged 9.3 g (20 mmol) of BisN-1 obtained above, 26 g (80 mmol) of cesium carbonate, 0.8 g (4 mmol) of copper iodide, 1.7 g (12 mmol) of dimethyl glycine hydrochloride and 80 mL of dioxane, 8.2 g (40 mmol) of iodobenzene was added thereto, the reaction liquid was stirred at 90° C. for 67 hours to perform a reaction. Then, 500 mL of ethyl acetate was added to precipitate a reaction product, and the resultant was cooled to room temperature followed by filtration for separation. The resulting solid was filtered and dried, and thereafter separated and purified by column chromatography to thereby provide 6.8 g of an objective compound (BisN-1-PH2) represented by the following formula.

BisN-1-PH2: δ (ppm) 6.8 to 8.0 (29H, Ph-H), 5.3 (1H, C—H)

(BisN-1-PH2)

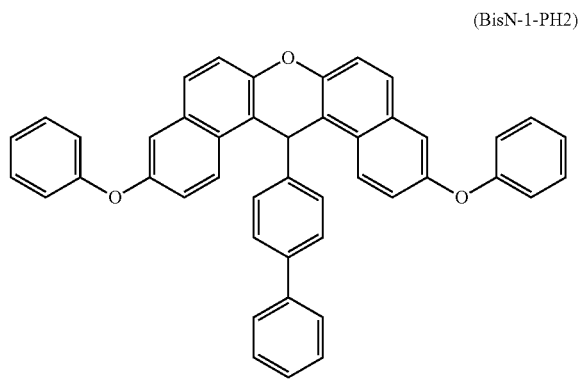 [SMILES: c1ccc(Oc2ccc3c4c(ccc3c2)Oc2ccc3cc(Oc5ccccc5)ccc3c2C4c2ccc(-c3ccccc3)cc2)cc1]

Herein, the molecular weight of BisN-1-PH1 obtained was 542. In addition, the carbon concentration and the oxygen concentration thereof were 86.3% by mass and 8.9% by mass, respectively.

The molecular weight of BisN-1-PH2 obtained was 618. In addition, the carbon concentration and the oxygen concentration thereof were 87.4% by mass and 7.8% by mass, respectively.

Production Example 1

To a four-neck flask having a bottom outlet and an inner volume of 10 L, equipped with a Dimroth condenser, a thermometer and a stirring blade were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 ml of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Thereafter, to a four-neck flask having an inner volume of 0.5 L, equipped with a Dimroth condenser, a thermometer and a stirring blade were charged 100 g (0.51 mol) of the dimethylnaphthaleneformaldehyde resin obtained in Production Example 1 and 0.05 g of paratoluenesulfonic acid under a nitrogen stream, and heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

Examples 1 to 4 and Comparative Example 1

BisN-1-CH1, BisN-1-CH2, BisN-1-PH1, BisN-1-PH2 and BisN-1 were subjected to a heat resistance test and a solubility test. The results are shown in Table 1.

Each material for forming an underlayer film for lithography, having composition shown in Table 1, was prepared. Then, such a material for forming an underlayer film was spin-coated on a silicon substrate, thereafter baked at 240° C. for 60 seconds and further at 400° C. for 120 seconds to prepare each underlayer film having a film thickness of 200 nm. The following acid generating agent, crosslinking agent and organic solvent were used.

Acid generating agent: di-tert-butyldiphenyliodonium nonafluoromethanesulfonate (DTDPI) (designated as "DTDPI" in Table.) produced by Midori Kagaku Co., Ltd.

Crosslinking agent: Nikalac MX270 (designated as "Nikalac" in Table.) produced by Sanwa Chemical Co., Ltd.

Organic solvent: cyclohexanone (designated as "CHN" in Table.)

[Etching Test]

Further, an etching test was performed under conditions shown below to evaluate etching resistance. The evaluation results are shown in Table 1.

Etching apparatus: RIE-10NR manufactured by Samco Inc.

Output: 50 W
Pressure: 20 Pa
Time: 2 min
Etching Gas

Ar gas flow rate: $CF_4$ gas flow rate: $O_2$ gas flow rate=50:5:5 (sccm)

[Evaluation of Etching Resistance]

The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (BisN-1-CH1) used in Example 1. Then, the etching test was performed with respect to the underlayer film of novolac, and the etching rate in that time was measured.

Then, the etching test was performed with respect to each underlayer film of Example 1 and Comparative Example 1, and the etching rate in that time was measured.

Then, the etching resistances were evaluated according to the following criteria based on the etching rate of the underlayer film of novolac. The results are shown in Table 1.

<Evaluation Criteria>

A; etching rate of less than −10% compared with the underlayer film of novolac

B; etching rate of −10% to +5% compared with underlayer film of novolac

C; etching rate of more than +5% compared with the underlayer film of novolac

Then, each solution of the materials for forming an underlayer film for lithography of Examples 1 to 4 and Comparative Example 1 including BisN-1-CH1, BisN-1-CH2, BisN-1-PH1, BisN-1-PH2 and BisN-1, respectively, was coated on a $SiO_2$ substrate having a film thickness of 300 nm, and baked at 240° C. for 60 seconds and further at 400° C. for 120 seconds, to form each underlayer film having a film thickness of 80 nm. A resist solution for ArF was coated on the underlayer film, and baked at 130° C. for 60 seconds to thereby form a photoresist layer having a film thickness of 150 nm. Herein, as the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

A compound of the following formula (11) was obtained by dissolving 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile in 80 mL of tetrahydrofuran, subjecting the resultant to polymerization under a nitrogen atmosphere for 22 hours with the reaction temperature being kept at 63° C., then dropping the reaction solution in 400 mL of n-hexane to solidify and purify a product resin, collecting a white powder produced, by filtration, and drying it under reduced pressure at 40° C. overnight.

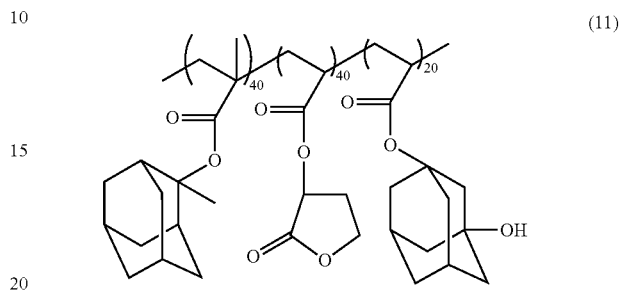

(11)

(in formula (11), the numerals 40, 40, and 20 indicate the proportions of the respective constituent units, and do not mean a block copolymer.)

Then, the photoresist layer was exposed with a mask by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

The shapes and defects of the resist patterns of 55 nm L/S (1:1) and 80 nm L/S (1:1) obtained were observed. The results are shown in Table 1.

Comparative Example 2

Except that CR-1 was used, the same manner as in Examples 1 to 4 and Comparative Example 1 was performed to prepare a material for forming an underlayer film. The material was spin-coated on a silicon substrate, and then baked at 240° C. for 60 seconds and further at 400° C. for 120 seconds, to produce an underlayer film having a film thickness of 200 nm. Thereafter, the etching resistance was evaluated. The results are shown in Table 1.

Comparative Example 3

Except that no underlayer film was formed, the same manner as in Examples 1 to 4 and Comparative Example 1 was performed to directly form a photoresist layer on a $SiO_2$ substrate, thereby providing a positive-type resist pattern. The evaluation results are shown in Table 1.

TABLE 1

| | Heat resistance | Solubility | Compound or resin (parts by mass) | Organic solvent (parts by mass) | Acid generating agent (parts by mass) | Crosslinking agent (parts by mass) | Etching resistance | Resolution (nmL/s) | Sensitivity (μC/cm$^2$) | Resist pattern formation after development |
|---|---|---|---|---|---|---|---|---|---|---|
| Example 1 | A | A | BisN-1-CH1 (5) | CHN (95) | DTDPI (0.25) | Nikalac (0.25) | A | 50 | 12 | Good |

TABLE 1-continued

| | Heat resistance | Solubility | Compound or resin (parts by mass) | Organic solvent (parts by mass) | Acid generating agent (parts by mass) | Cross-linking agent (parts by mass) | Etching resistance | Resolution (nmL/s) | Sensitivity (μC/cm$^2$) | Resist pattern formation after development |
|---|---|---|---|---|---|---|---|---|---|---|
| Example 2 | A | A | BisN-1-CH2 (5) | CHN (95) | DTDPI (0.25) | Nikalac (0.25) | A | 50 | 12 | Good |
| Example 3 | A | A | BisN-1-PH1 (5) | CHN (95) | DTDPI (0.25) | Nikalac (0.25) | A | 50 | 12 | Good |
| Example 4 | A | A | BisN-1-PH2 (5) | CHN (95) | DTDPI (0.25) | Nikalac (0.25) | A | 50 | 12 | Good |
| Comparative Example 1 | A | C | BisN-1 (5) | CHN (95) | DTDPI (0.25) | Nikalac (0.25) | A | 55 | 12 | Poor |
| Comparative Example 2 | — | — | CR-1 (5) | CHN (95) | DTDPI (0.25) | Nikalac (0.25) | C | — | — | — |
| Comparative Example 3 | — | — | (No underlayer film formed) | | | | | 80 | 26 | Poor |

As can be seen from Table 1, it was confirmed that all of heat resistance, solubility and etching resistance were good in Example 1 in which BisN-1-CH1 was used, in Example 2 in which BisN-1-CH2 was used, in Example 3 in which BisN-1-PH1 was used and in Example 4 in which BisN-1-PH2 was used, such compounds being compounds satisfying the configuration of the present embodiment. On the other hand, heat resistance and etching resistance were good, but solubility was poor in Comparative Example 1 in which the polyphenol compound BisN-1 was used. In addition, etching resistance was poor in Comparative Example 2 in which CR-1 (phenol-modified dimethylnaphthaleneformaldehyde resin (CR-1) was used.

In addition, it was confirmed that the resist pattern shape after development was good and no defects were observed in Examples 1 to 4. On the other hand, it was confirmed that the resist pattern shape after development was poor and many defects were also observed in Comparative Example 1. The reason was presumed as follows: BisN-1 used in Comparative Example 1 had a low solubility in the coating solvent.

Furthermore, it was confirmed that resolution and sensitivity were significantly excellent in Examples 1 to 4 as compared with Comparative Example 3 in which underlayer film formation was omitted.

It was indicated from the difference in resist pattern shape after development that the material for forming an underlayer film for lithography in each of Examples 1 to 4 was good in adhesiveness with a resist material.

Example 5

Then, the solution of the material for forming an underlayer film for lithography used in Example 1 was coated on a SiO$_2$ substrate having a film thickness of 300 nm, and baked at 240° C. for 60 seconds and further at 400° C. for 120 seconds to thereby form an underlayer film having a film thickness of 80 nm. A silicon-containing intermediate layer material was coated on the underlayer film, and baked at 200° C. for 60 seconds to thereby form an intermediate layer film having a film thickness of 35 nm. Furthermore, the resist solution for ArF was coated on the intermediate layer film, and baked at 130° C. for 60 seconds to thereby form a photoresist layer having a film thickness of 150 nm. Herein, as the silicon-containing intermediate layer material, the silicon atom-containing polymer described in <Synthesis Example 1> in Japanese Patent Laid-Open No. 2007-226170 was used.

Then, the photoresist layer was exposed with a mask by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern of 55 nm L/S (1:1).

Thereafter, dry etching processing of a silicon-containing intermediate layer film (SOG) was performed by using RIE-10NR manufactured by Samco Inc. with the obtained resist pattern as a mask, and subsequently, dry etching processing of an underlayer film and dry etching processing of a SiO$_2$ film were sequentially performed with the obtained silicon-containing intermediate layer film pattern as a mask and the obtained underlayer film pattern as a mask, respectively.

Respective etching conditions are as shown below.

Etching Conditions of Resist Intermediate Layer Film with Resist Pattern
Output: 50 W
Pressure: 20 Pa
Time: 1 min
Etching gas
Ar gas flow rate:CF$_4$ gas flow rate:O$_2$ gas flow rate=50:8:2 (sccm)

Etching Conditions of Resist Underlayer Film with Resist Intermediate Film Pattern
Output: 50 W
Pressure: 20 Pa
Time: 2 min
Etching gas
Ar gas flow rate:CF$_4$ gas flow rate:O$_2$ gas flow rate=50:5:5 (sccm)

Etching Conditions of SiO$_2$ Film with Resist Underlayer Film Pattern
Output: 50 W
Pressure: 20 Pa
Time: 2 min
Etching gas
Ar gas flow rate:C$_5$F$_{12}$ gas flow rate:C$_2$F$_6$ gas flow rate:O$_2$ gas flow rate=50:4:3:1 (sccm)

The pattern cross-section (the shape of the SiO$_2$ film after etching) in Example 5, obtained as above, was observed by using an electron microscope (S-4800) manufactured by Hitachi Ltd. As a result, it was confirmed that Example 5 in which the underlayer film satisfying the configuration of the present embodiment was used was good because the shape of the SiO$_2$ film after etching in multilayer resist processing was rectangular and no defects were observed.

As described above, the present invention is not limited to the embodiments and Examples, and can be appropriately modified without departing from the gist thereof.

The compound and the resin of the present invention have a relatively high carbon concentration, a relatively low oxygen concentration, a relatively high heat resistance and a high solvent solubility, can be applied to a wet process, and therefore can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film. In particular, the present invention can be particularly effectively utilized in the field of an underlayer film for lithography and an underlayer film for a multilayer resist.

The invention claimed is:

1. A material for forming an underlayer film for lithography comprising:

a compound represented by the following formula (1):

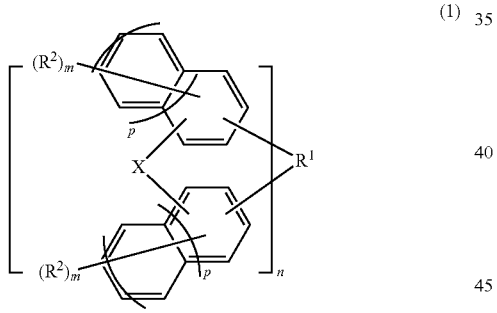

(1)

wherein each X is an oxygen atom, R$^1$ represents a 2n-valent group having 1 to 30 carbon atoms, the group may have an alicyclic hydrocarbon group, a double bond, a hetero atom, or an aryl group having 6 to 30 carbon atoms, each R$^2$ independently represents a straight, branched or cyclic alkyl group having 1 to 10 carbon atoms, an aryl group having 6 to 10 carbon atoms, an alkenyl group having 2 to 10 carbon atoms, an alkoxy group having 1 to 30 carbon atoms, an aryloxy group having 6 to 30 carbon atoms, or a hydroxyl group, in which at least one R$^2$ is selected from the group consisting of a butoxy group, a pentyloxy group, a hexyloxy group, a cyclobutyloxy group, a cyclopentyloxy group, a cyclohexyloxy group, a cyclohexenyloxy group, an isophoronyloxy group, a norbornanyloxy group, an adamantyloxy group, a tricyclodecanyloxy group, a pyridinyloxy group, a phenyloxy group, a methylphenyloxy group, a dimethylphenyloxy group, a trimethylphenyloxy group, an ethylphenyloxy group, a propylphenyloxy group, a butylphenyloxy group, a cyclohexylphenyloxy group, a fluorophenyloxy group, a bromophenyloxy group, an iodophenyloxy group, a hydroxyphenyloxy group, a methoxyphenyloxy group, an aminophenyloxy group, a nitrophenyloxy group, a cyanophenyloxy group, a phenylphenyloxy group, a terphenyloxy group, a phenyloxyphenyloxy group, a naphthyloxy group, a methylnaphthyloxy group, a dimethylnaphthyloxy group, an ethylnaphthyloxy group, a fluoronaphthyloxy group, a chloronaphthyloxy group, a bromonaphthyloxy group, an iodonaphthyloxy group, a hydroxynaphthyloxy group, a methoxynaphthyloxy group, an aminonaphthyloxy group, a nitronaphthyloxy group, a cyanonaphthyloxy group, a phenylnaphthyloxy group, a phenyloxynaphthyloxy group, an anthracenyloxy group, a pyrenyloxy group, a methylpyrenyloxy group, a dimethylpyrenyloxy group and a fluorenyloxy group, each m is independently an integer of 1 to 6, each p is 1, and n is an integer of 1 to 4, the compound having a solubility of 5% by mass or more in cyclohexanone;

cyclohexanone as an organic solvent; and at least one of an acid generating agent and a crosslinking agent.

2. The material for forming an underlayer film for lithography according to claim 1, wherein the compound represented by the formula (1) is a compound represented by the following formula (1A-2):

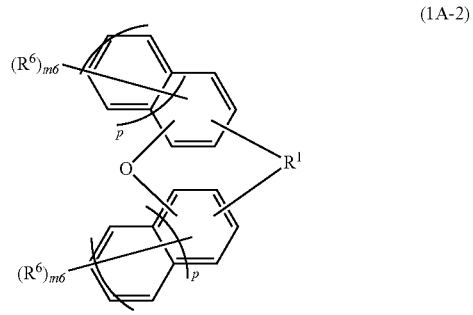

(1A-2)

wherein R$^1$ and p are the same as those described in formula (1), R$^6$ is the same as R$^2$ defined in the formula (1), and each m$^6$ is independently an integer of 1 to 3.

3. The material for forming an underlayer film for lithography according to claim 1, wherein the compound represented by formula (1) is represented by the following formula (BisN-1-CH1) or the following formula (BisN-1-CH2)

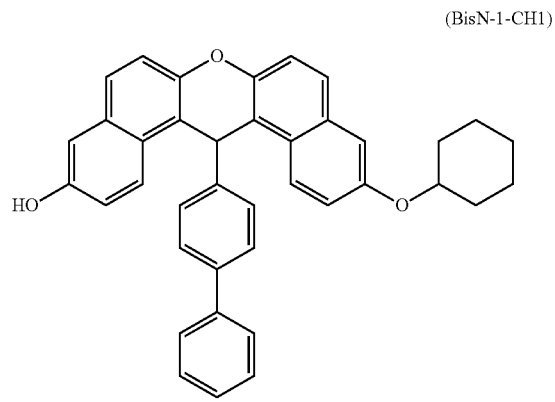

(BisN-1-CH1)

-continued (BisN-1-CH2)

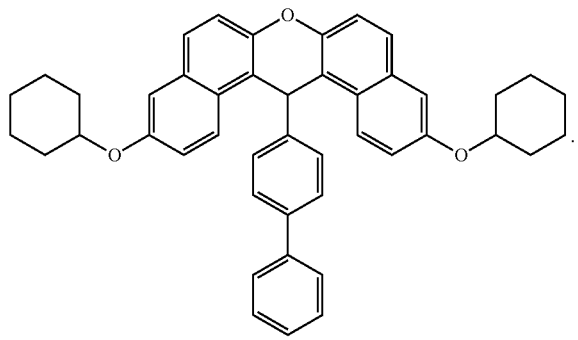

4. The material for forming an underlayer film for lithography according to claim 1, wherein the compound represented by formula (1) is represented by the following formula (BisN-1-PH1) or the following formula (BisN-1-PH2)

(BisN-1-PH1)

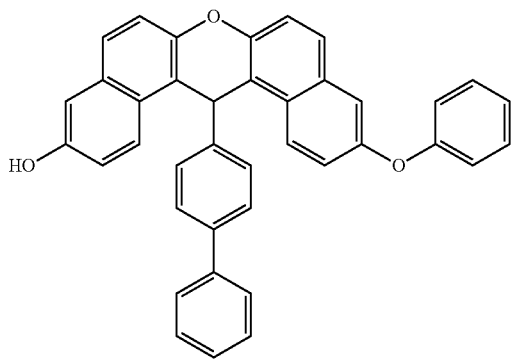

(BisN-1-PH2)

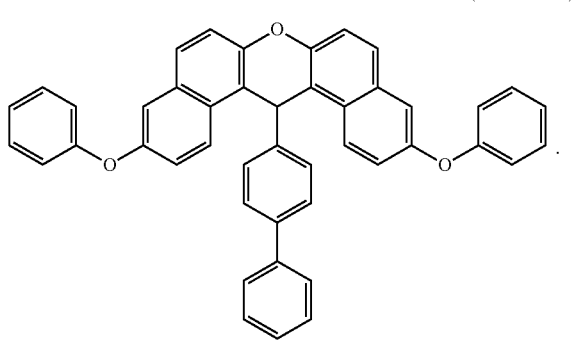

5. The material for forming the underlayer film for lithography according to claim 1 comprising the acid generating agent.

6. The material for forming the underlayer film for lithography according to claim 1 comprising the crosslinking agent.

7. The material for forming an underlayer film for lithography according to claim 1, wherein (i) a content of the organic solvent is 100 to 10,000 parts by mass based on 100 parts by mass of the compound, (ii) when the material for forming the underlayer film for lithography comprises the acid generating agent, a content of the acid generating agent is 0.1 to 50 parts by mass based on 100 parts by mass of the compound, and (iii) when the material for forming the underlayer film for lithography comprises the crosslinking agent, a content of the crosslinking agent is 5 to 50 parts by mass based on 100 parts by mass of the compound.

8. The material for forming an underlayer film for lithography according to claim 1, wherein the crosslinking agent is at least one selected from the group consisting of aldehyde, ketone, carboxylic acid, carboxylic halide, a halogen-containing compound, an amino compound, an imino compound, isocyanate and an unsaturated hydrocarbon group-containing compound.

9. An underlayer film for lithography, formed from the material for forming the underlayer film for lithography according to claim 1.

10. A resist pattern forming method, comprising
    step (A-1) of forming an underlayer film on a substrate by using the material for forming the underlayer film for lithography according to claim 1,
    step (A-2) of forming at least one photoresist layer on the underlayer film, and
    step (A-3) of, after step (A-2), irradiating a predetermined region of the photoresist layer with radiation, followed by developing.

11. A circuit pattern forming method, comprising
    step (B-1) of forming an underlayer film on a substrate by using the material for forming the underlayer film for lithography according to claim 1,
    step (B-2) of forming an intermediate layer film on the underlayer film by using a silicon atom-containing resist intermediate layer film material,
    step (B-3) of forming at least one photoresist layer on the intermediate layer film,
    step (B-4) of, after step (B-3), irradiating a predetermined region of the photoresist layer with radiation, followed by developing to form a resist pattern, and
    step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

* * * * *

UNITED STATES PATENT AND TRADEMARK OFFICE
CERTIFICATE OF CORRECTION

PATENT NO. : 10,745,372 B2
APPLICATION NO. : 15/539560
DATED : August 18, 2020
INVENTOR(S) : Takumi Toida et al.

Page 1 of 2

It is certified that error appears in the above-identified patent and that said Letters Patent is hereby corrected as shown below:

In the Claims

Column 67, Lines (35-45):

In Claim 1, please delete " 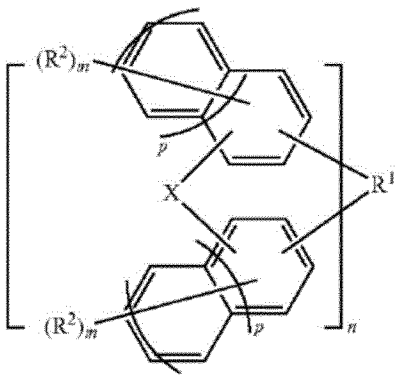 " and insert

-- 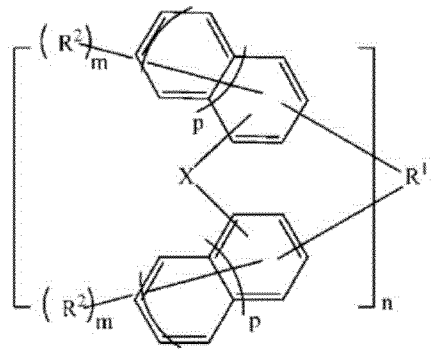 --, therefor.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,745,372 B2

Column 68, Lines (30-40):

In Claim 2, please delete " 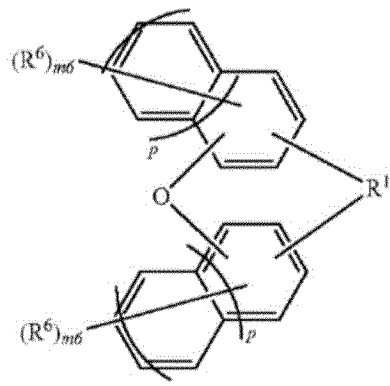 " and insert

-- 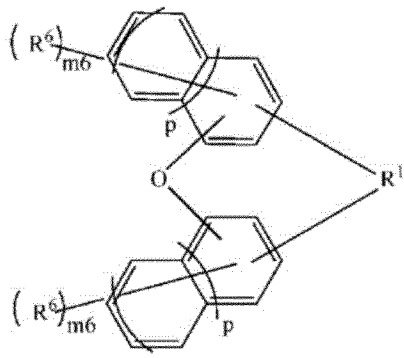 --, therefor.